(12) United States Patent
Wolfe et al.

(10) Patent No.: US 11,793,103 B2
(45) Date of Patent: Oct. 24, 2023

(54) METHODS AND APPARATUSES FOR TREATING AGRICULTURAL MATTER

(71) Applicant: Applied Quantum Engeries, LLC, Naples, FL (US)

(72) Inventors: Benjamin Wolfe, Naples, FL (US); George Paskalov, Torrance, CA (US); Rick Jarvis, Naples, FL (US); Jerzy P. Puchacz, Pleasanton, CA (US)

(73) Assignee: APPLIED QUANTUM ENERGIES, LLC, Naples, FL (US)

( * ) Notice: Subject to any disclaimer, the term of this patent is extended or adjusted under 35 U.S.C. 154(b) by 1073 days.

(21) Appl. No.: 16/571,244

(22) Filed: Sep. 16, 2019

(65) Prior Publication Data
US 2020/0015344 A1    Jan. 9, 2020

Related U.S. Application Data

(62) Division of application No. 15/019,313, filed on Feb. 9, 2016, now Pat. No. 10,420,199.
(Continued)

(51) Int. Cl.
*H05H 1/24* (2006.01)
*A01C 1/08* (2006.01)
(Continued)

(52) U.S. Cl.
CPC .............. *A01C 1/08* (2013.01); *A01C 1/00* (2013.01); *A61L 2/14* (2013.01); *H01J 37/32* (2013.01);
(Continued)

(58) Field of Classification Search
CPC .... A01C 1/08; A01C 1/00; A23B 9/02; A23B 9/025
See application file for complete search history.

(56) References Cited

U.S. PATENT DOCUMENTS 2,422,019 A * 6/1947 Kemp .................. A01C 1/08
366/318
3,146,730 A    9/1964 White
(Continued)

FOREIGN PATENT DOCUMENTS

DE    102004050493 A1    4/2006
GB         2227639          8/1990
(Continued)

OTHER PUBLICATIONS

Bormashenko, Edward et al.; Cold Radiofrequency Plasma Treatment Modifies Wettability and Germination Speed of Plant Seeds; Scientific Reports 2:741; Oct. 17, 2012.
(Continued)

*Primary Examiner* — Christopher D Hutchens
(74) *Attorney, Agent, or Firm* — Squire Patton Boggs US LLP

(57) ABSTRACT

Methods and apparatuses to activate, modify, and sanitize the surfaces of granular, powdered, or seed material placed in a continuous flow of a low-temperature, reduced-pressure gas plasma. Said plasma may be created with radio-frequency power, using capacitive-inductive, or a combination of both types of discharge. The plasma is generated at pressures in the 0.01 to 10 Torr range. RF frequency ranges from 0.2 to 220 MHz, and correspond to a plasma density between about $n_e \times 10^8$-$n_e \times 10^{12}$ or 0.001 to 0.4 W/cm$^3$. Inserts and electrodes may be temperature controlled to control process conditions. RF discharge may be pulsed or modulated by different frequency in order to stimulate energy exchange between gas plasma and process material. The apparatuses may be grounded, biased and mechanically activated (e.g., vibration, rotation, etc.).

20 Claims, 18 Drawing Sheets

Related U.S. Application Data

(60) Provisional application No. 62/113,819, filed on Feb. 9, 2015.

(51) Int. Cl.
  *A61L 2/14* (2006.01)
  *H05H 1/46* (2006.01)
  *A01C 1/00* (2006.01)
  *H01J 37/32* (2006.01)
  *A23B 9/02* (2006.01)
  *A23B 9/18* (2006.01)

(52) U.S. Cl.
  CPC .............. *H05H 1/46* (2013.01); *A23B 9/02* (2013.01); *A23B 9/025* (2013.01); *A23B 9/18* (2013.01); *A61L 2202/16* (2013.01); *H05H 1/466* (2021.05); *H05H 2242/26* (2021.05)

(56) References Cited

U.S. PATENT DOCUMENTS

| | | | |
|---|---|---|---|
| 4,320,715 A * | 3/1982 | Maloney | B01F 25/742 |
| | | | 427/221 |
| 4,633,611 A * | 1/1987 | Schiller | A01C 1/08 |
| | | | 47/1.3 |
| 4,921,674 A * | 5/1990 | Enos | A01C 1/08 |
| | | | 47/DIG. 9 |
| 4,974,334 A | 12/1990 | Roddewig | |
| 5,281,315 A | 1/1994 | Krapivina et al. | |
| 5,527,760 A * | 6/1996 | Rensing | B01J 2/006 |
| | | | 47/57.6 |
| 6,096,564 A | 8/2000 | Denes et al. | |
| 6,543,460 B1 | 4/2003 | Denes et al. | |
| 6,615,538 B2 | 9/2003 | Hittin | |
| 6,745,512 B1 * | 6/2004 | Panzer | A01C 1/00 |
| | | | 47/1.3 |
| 6,923,886 B2 | 8/2005 | Brum | |
| 8,221,679 B2 | 7/2012 | Golkowski | |
| 8,309,033 B2 | 11/2012 | Finn et al. | |
| 8,381,438 B2 | 2/2013 | Fytagoras | |
| 8,771,595 B2 | 7/2014 | Paskalov | |
| 2006/0081567 A1 | 4/2006 | Dougherty et al. | |
| 2008/0145553 A1 | 6/2008 | Boulos | |
| 2008/0276591 A1 | 11/2008 | Tippery et al. | |
| 2011/0039036 A1 | 2/2011 | Reichen | |
| 2011/0297532 A1 | 12/2011 | Chakraborty et al. | |
| 2012/0145041 A1 | 6/2012 | Walters | |
| 2012/0244266 A1 * | 9/2012 | Ku | A23B 9/08 |
| | | | 426/419 |
| 2013/0320274 A1 | 12/2013 | Walters | |
| 2014/0076861 A1 | 3/2014 | Cornelius | |
| 2014/0144877 A1 | 5/2014 | DeLarge | |
| 2015/0101082 A1 | 4/2015 | Bormashenko et al. | |
| 2015/0327430 A1 | 11/2015 | Dong et al. | |
| 2016/0374261 A1 * | 12/2016 | Rögner | H01J 37/06 |
| | | | 422/186.05 |

FOREIGN PATENT DOCUMENTS

| | | |
|---|---|---|
| RU | 2076555 | 4/1997 |
| RU | 2246814 | 2/2005 |
| WO | 2012112042 | 8/2012 |
| WO | 2013090340 | 6/2013 |
| WO | 2013090418 | 6/2013 |
| WO | 2013168038 | 11/2013 |

OTHER PUBLICATIONS

Ling, Li et al.; Effects of cold plasma treatment on seed germination and seedling growth of soybean; Scientific Reports 4:5859; Jul. 31, 2014.

Jiang, Jiafeng; Effect of Cold Plasma Treatment on Seed Germination and Growth of Wheat; Plasma Science and Technology, vol. 16, No. 1; Jan. 2014.

Mitra, Anindita et al.; Inactivation of Surface-Borne Microorganisms and Increased Germination of Seed Specimen by Cold Atmospheric Plasma; Food Biopress Technol (Springerlink.com); May 9, 2013.

Jiang, Jiafeng; Effect of Seed Treatment by Cold Plasma on the Resistance of Tomato to Ralstonia solanacearum (Bacterial Wilt); Plos One; vol. 9, Issue 5 (www.plosone.org); May 2014.

Volin, John et al.; Modification of Seed Germination Performance through Cold Plasma Chemistry Technology; https://dl.sciencesocieties.org/publications/cs/abstracts/40/6/1706; Oct. 13, 1999.

Flatova, I. et al.; The Effect of Plasma Treatment of Seeds of Some Grain and Legumes on Their Sowing Quality and Productivity; Paper presented at the 15th International Conference on Plasma Physics and Applications, Jul. 1, 2010.

* cited by examiner

METHODS AND APPARATUSES FOR TREATING AGRICULTURAL MATTER

CROSS REFERENCE TO RELATED APPLICATION

This application is a divisional of U.S. patent application Ser. No. 15/019,313, filed on Feb. 9, 2016, which in turn claims the benefit of U.S. Provisional Patent Application No. 62/113,819, filed on Feb. 9, 2015. The disclosures of both of these applications are incorporated by reference herein in their entirety.

FIELD OF INVENTION

The present disclosure is directed to methods and apparatuses used in the treatment of matter. More particularly, the present disclosure is directed to methods for treating agricultural matter, such as seeds, with plasma. Further, the present disclosure is directed to apparatuses for treating agricultural matter with plasma.

BACKGROUND

Treating agricultural matter for sanitation and germination purposes is known. Known treatments include washing, scrubbing, and applying substances (e.g., powder) to agricultural matter. The treatments may be modified to produce various activation, modification, and sanitization results.

SUMMARY OF THE INVENTION

In one embodiment, a treatment module comprises an airtight cylindrical housing comprising an external wall and an internal chamber, the housing having a structural integrity to withstand a low-pressure environment, at least one inlet for loading plant seeds into the chamber, wherein the inlet is sealable and distal to the chamber, and at least one port for creating a low-pressure environment substantially free of gas and introducing gas into the chamber. The treatment module further comprises at least one plasma generator, selected from the group consisting of an electrode pair, a coil, and electrode pair and coil, for creating a plasma from gas introduced into the chamber, a plurality of discs, disposed substantially linearly within the chamber, and at least one egress for unloading plant seeds from the chamber, wherein the egress is sealable and distal to the chamber.

In another embodiment, an apparatus comprises a hopper having an upper opening, a lower opening, and at least one side wall that connects the upper and lower openings, an elongated, airtight seed-processing chamber that receives seeds fed through the hopper, a load lock seal, disposed between the hopper and the airtight chamber, a vacuum, operably connected to the chamber, for removing gas from the chamber, and a gas supply, operably connected to the chamber, for delivering gas to the chamber. The apparatus further comprises at least one pair of electrodes, disposed about the chamber, capable of generating a plasma environment, a temperature regulator comprising a temperature sensor, a temperature control unit, a temperature control element, a plurality of first inserts, disposed in the chamber, each first insert having an annular passage and a cross sectional area that substantially coincides with the cross sectional area of the chamber, a plurality of second inserts, disposed in the chamber, each second insert having apertures and a cross sectional area that substantially coincides with the cross sectional area of the chamber, and an outlet, through which seeds processed in the chamber pass, and a load lock seal, disposed between the chamber and the outlet.

In a different embodiment, a method for treating agricultural matter comprises providing seeds to a cascading treatment apparatus, introducing seeds into a chamber in the cascading treatment apparatus, hindering the vertical flow of seeds within the chamber with encumbrance structures, evacuating gas from the chamber, introducing gas to the chamber, ionizing gas introduced into the chamber, monitoring and regulating ionizing energy within the chamber, and monitoring and regulating temperature within the chamber. The method may further comprise the steps of introducing seeds into a second chamber in the cascading treatment apparatus, hindering the vertical flow of seeds within the second chamber with encumbrance structures, evacuating gas from the second chamber, introducing gas to the second chamber, ionizing gas introduced into the second chamber, and monitoring and regulating temperature within the second chamber.

For apparatuses and methods used for treating seeds, a wide variety of seeds may be used. In one embodiment, the seeds are broadcasting- or row-crop seeds. In another embodiment, the seeds are selected from the group consisting of sorghum, tomato, corn, and alfalfa.

BRIEF DESCRIPTION OF THE DRAWINGS

In the accompanying drawings, structures are illustrated that, together with the detailed description provided below, describe exemplary embodiments of the claimed invention. Like elements are identified with the same reference numerals. It should be understood that elements shown as a single component may be replaced with multiple components, and elements shown as multiple components may be replaced with a single component. The drawings are not to scale and the proportion of certain elements may be exaggerated for the purpose of illustration. For the methods disclosed, the steps described need not be performed in the same sequence discussed or with the same degree of separation. Likewise, various steps may be omitted, repeated, or combined, as necessary, to achieve the same or similar objectives

FIG. 2a is a perspective view of an embodiment of the temperature control element shown in FIG. 1a;

FIG. 2b is a front elevational view of an alternative embodiment of the temperature control element shown in FIG. 2a;

FIG. 2c is a isometric view of an alternative embodiment of the temperature control element shown in FIG. 2a;

DETAILED DESCRIPTION

The following includes definitions of selected terms employed herein. The definitions include various examples and/or forms of components that fall within the scope of a term and that may be used for implementation. The examples are not intended to be limiting. Both singular and plural forms of terms may be within the definitions.

"Etching" refers to a process for removing a layer of material from the surface of an object.

"Surface activation," when used in conjunction with plasma treatments, refers to increasing the reactive properties (e.g. hydrophilic properties) on an object's surface.

While similar terms used in the following descriptions describe similar components, it is understood that because the terms carry slightly different connotations, one of ordinary skill in the art would not consider any one of the following terms to be purely interchangeable with any other term used to describe a common component.

Figure 1A:
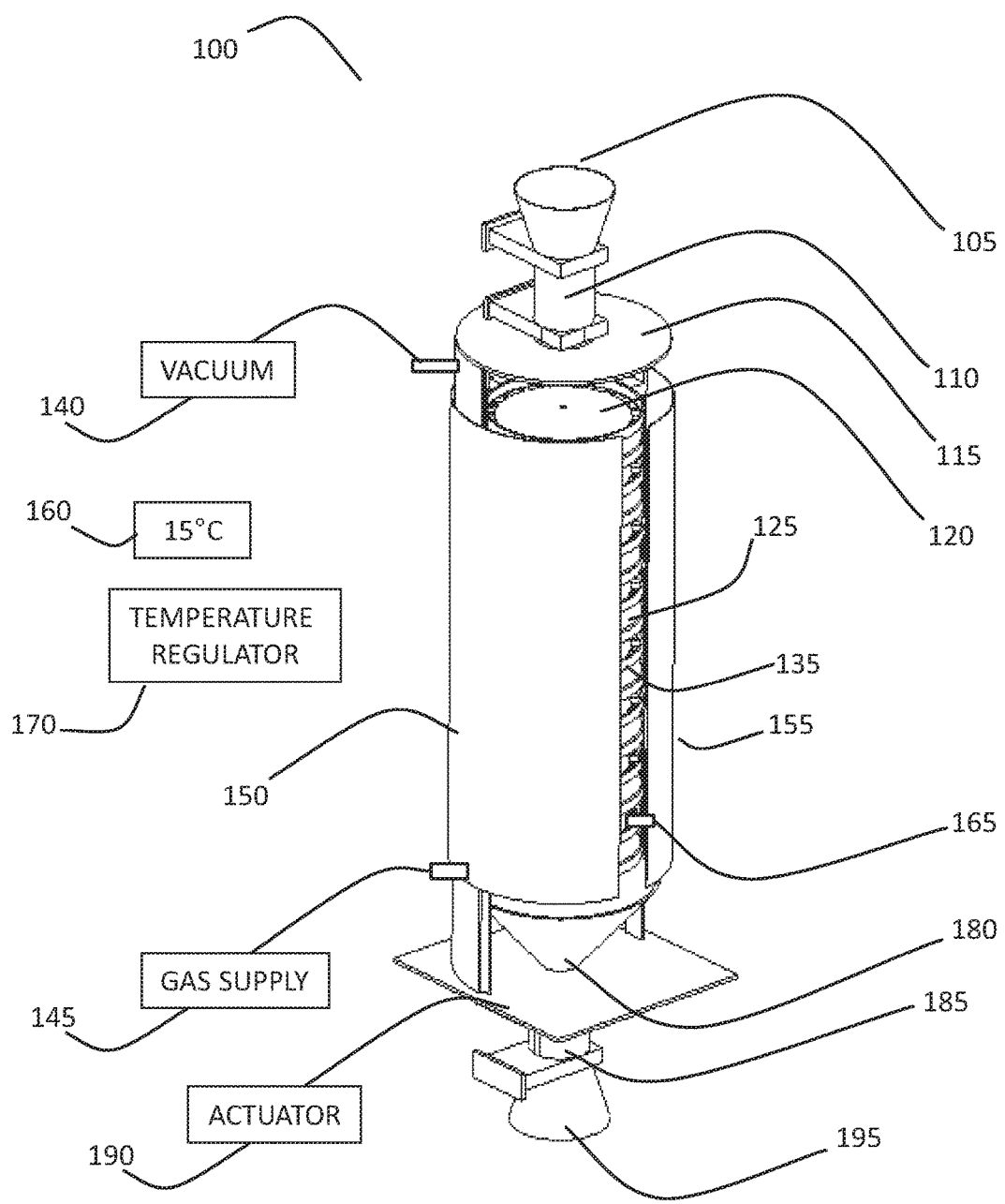
FIG. 1a is a perspective view of one embodiment of a treatment apparatus.

FIG. 1a is a perspective view of one embodiment of a treatment apparatus 100. The treatment apparatus 100 includes a hopper 105. Agricultural matter for treatment is placed in hopper 105. As shown, hopper 105 is a cone with an upper opening, a lower opening, and a side wall that connects the upper and lower openings. In an alternative embodiment (not shown), the hopper is pyramidal. In another alternative embodiment, the hopper can be made airtight.

Hopper 105 connects to load lock seal 110 and chamber 120. Load lock seal 110 allows agricultural matter from hopper 105 to travel to chamber 120 without breaking vacuum conditions in chamber 120. In an alternative embodiment (not shown), a valve, such as a four-way valve, replaces the load lock seal. It should be understood that many valves are suitable. Examples of suitable valves include without limitation, quarter-turn valves, sliding gate valves, and solenoid valves all applicable valves.

Apparatus 100 further comprises a housing 115 that surrounds chamber 120. Housing 115 supports an airtight cylinder that defines the boundaries of chamber 120. In an alternative embodiment (not shown), the housing does not define the boundaries of the chamber. As an example, additional components could be disposed between the housing and the chamber. In additional embodiments, the housing and/or chamber are prisms. In further embodiments, the housing includes an energy shield. As one of ordinary skill in the art will understand, a variety of shapes may be used for the housing and/or chamber.

As shown, a plurality of first inserts 125 are disposed within chamber 120. The first inserts 125 are circular and have a diameter that substantially coincides with the cross-sectional area of chamber 120. The diameter of the first inserts 125 substantially coincides with the cross-sectional area of chamber 120 such that agricultural matter cannot pass between the edge of the first inserts 125 and a chamber wall. In an alternative embodiment (not shown), the first inserts have a cross-sectional area between about 75-95% of the cross-sectional area of the chamber. In another embodiment, the first inserts have a cross-sectional area between about 50-70% of the cross-sectional area of the chamber.

Figure 2A:
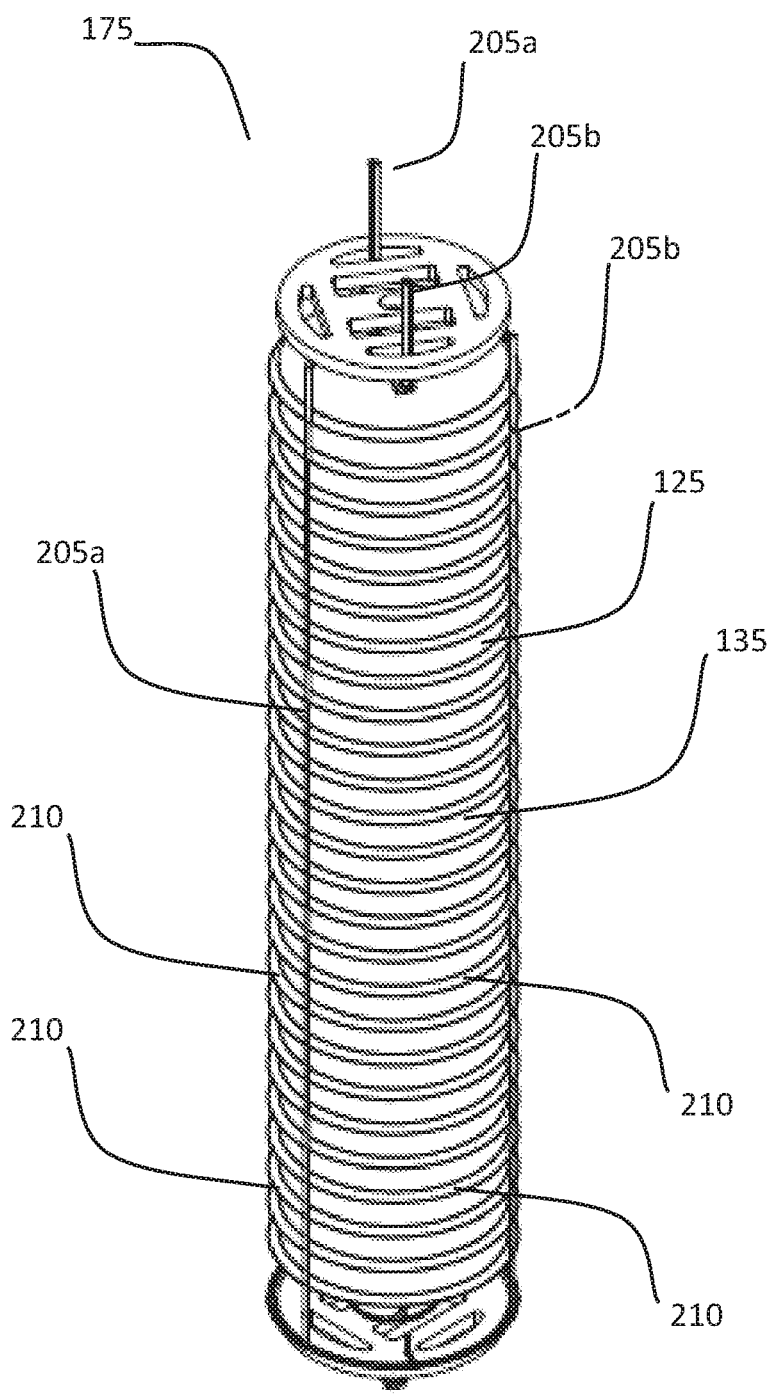
Figure 2B:
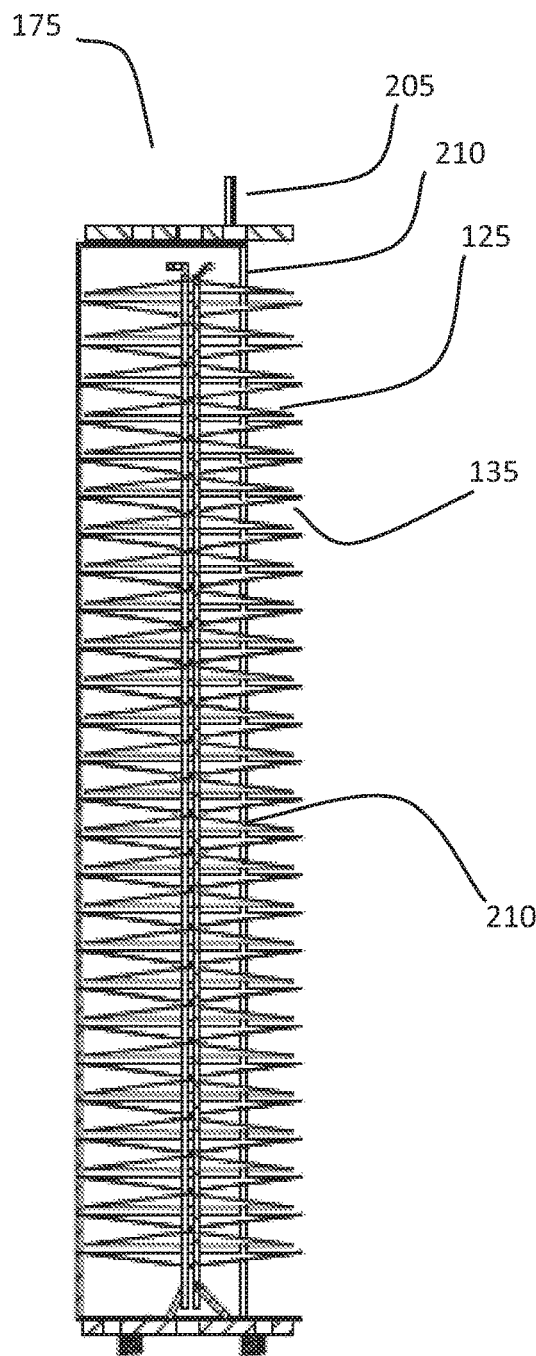
Figure 2C:
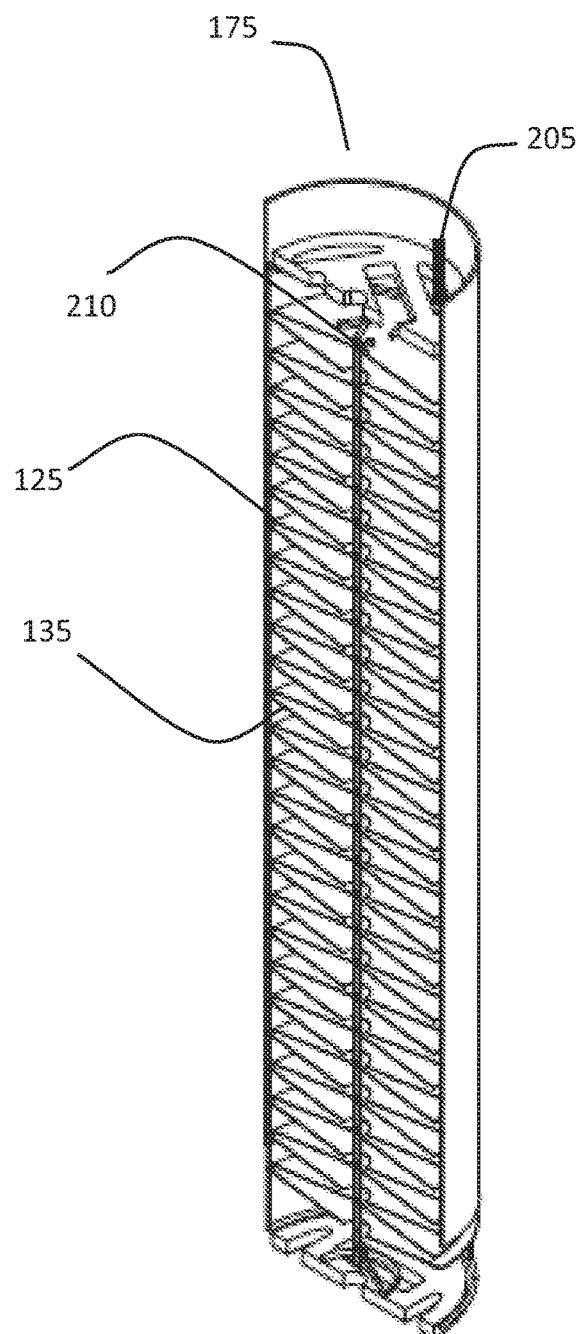
Figure 2D:
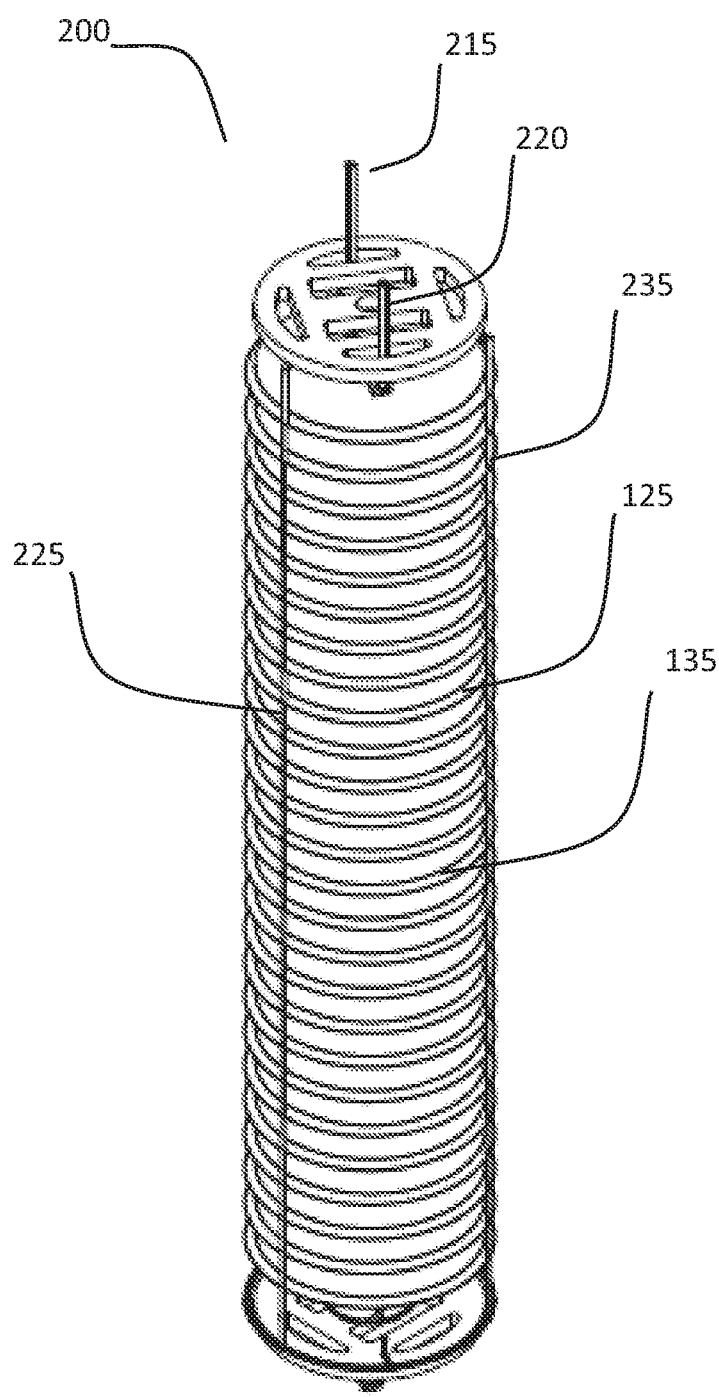
FIG. 2d is a perspective view of select components of an alternative embodiment of a treatment apparatus.
Figure 2E:
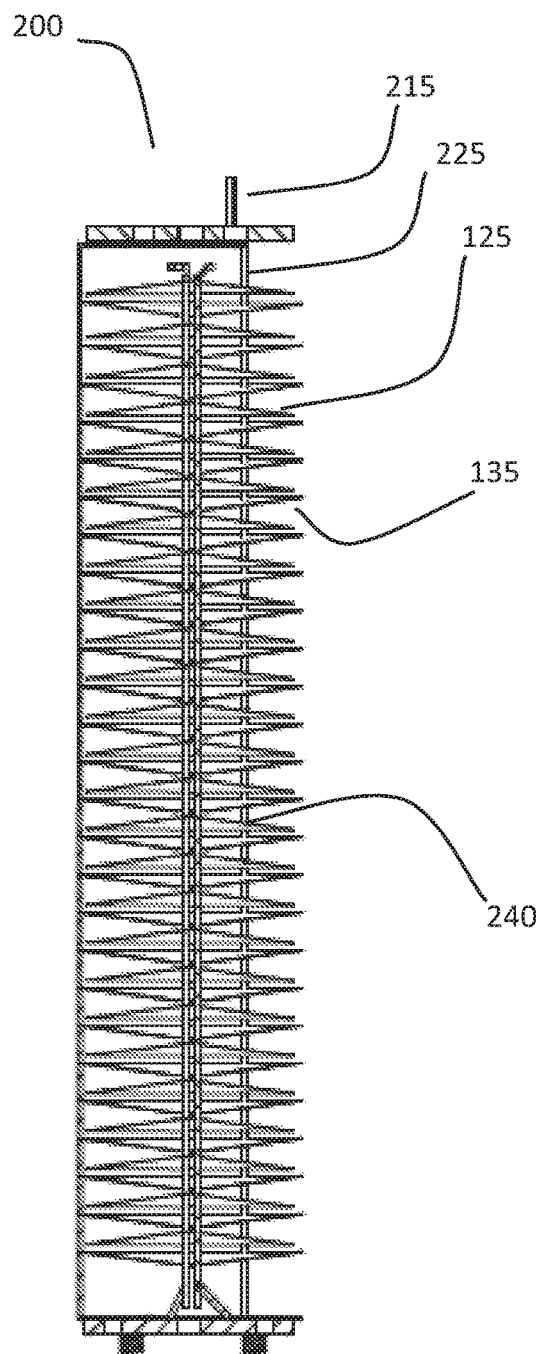
FIG. 2e is an alternative embodiment of the components shown in FIG. 2d.

In one embodiment, the first inserts 125 are inclined or angled with respect to the horizon (FIG. 2b and FIG. 2e depict inclined inserts). Suitable inclination angles include, without limitation, 5-60° with respect to the horizon. In an alternative embodiment (not shown), only a portion of a first insert is inclined. In another embodiment, a first insert is curved with respect to a horizontal plane.

Figure 1B:
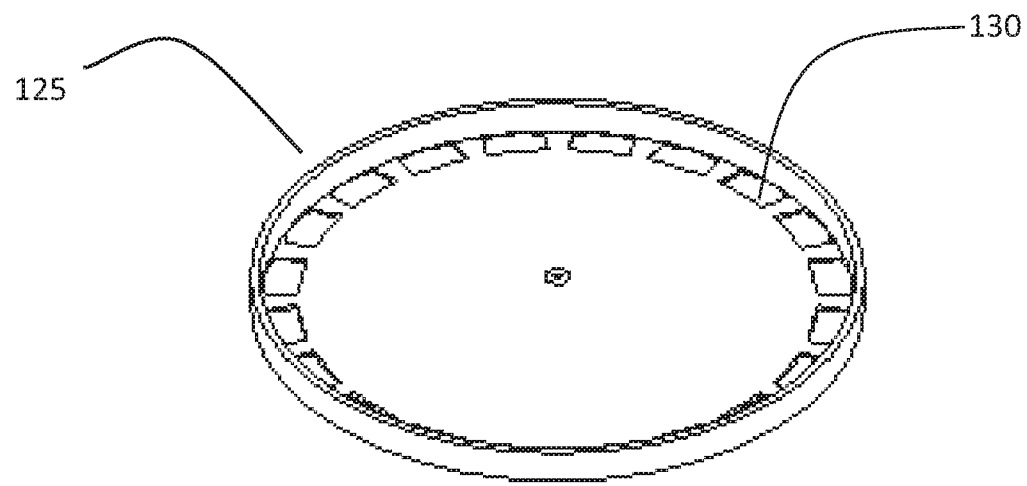
FIG. 1b is a perspective view of one embodiment of an insert with an aperture.

The first inserts 125 feature apertures 130 (as shown in FIG. 1b). Agricultural matter passes through apertures 130 as its progresses through chamber 120. As one of ordinary skill in the art will understand, a wide variety of cross-sectional shapes are suitable for apertures 130. Additionally, apertures 130 can be tuned to accommodate different applications. For example, the cross sectional area of aperture 130 can be decreased to slow the passage of material through chamber 120. Conversely, the cross sectional area of apertures 130 can be increased to promote the passage of material through chamber 120. In the embodiment shown in FIG. 1a, apertures 130 are disposed at the edges of the first inserts 125. In an alternative embodiment (not shown), the apertures are disposed on an interior portion of the plates. In additional alternative embodiments, apertures are scattered across the inserts. In another embodiment, the apertures are omitted so that the apparatus lacks apertures and only has edges allowing agricultural matter to spill off an edge.

Figure 1C:
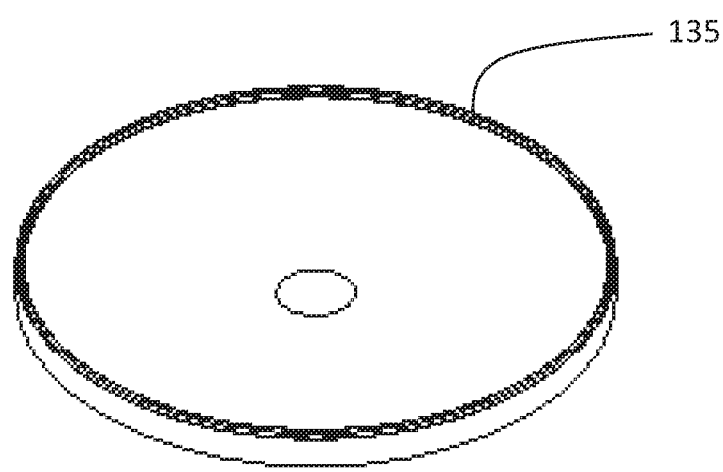
FIG. 1c is a perspective view of one embodiment of an insert.

In addition to the first inserts 125, a plurality of second inserts 135 are disposed within chamber 120. As shown in FIG. 1c, the second inserts 135 are inclined or curved and contain an inner ring that allows agricultural matter to pass through chamber 120 near the center (i.e., the core) of the chamber. When the first inserts 125 and the second inserts 135 are both curved, the second inserts 135 may be curved opposite of the first inserts 125. In another embodiment (not shown), the second inserts are flat.

In FIG. 1a, first and second inserts 125,135 are arranged in alternating fashion. When the first and second inserts are inclined and interspersed, material is directed between the periphery and the core of the apparatus 100 as it proceeds through the apparatus. In embodiments where the inserts are flat, movement produced by, without limitation, vibration, rocking, or gas diffusion, is used to direct material to proceed through the apparatus. For embodiments utilizing mechanical movement, an axis running through the apparatus could be used as a driving shaft for the mechanical motion. Additionally, mechanical arms or appendages may be used to direct material over the inserts or through the chamber.

The first and second inserts are not permanently attached as to allow for removal and maintenance. The first and second inserts may be made from a variety of materials, including, without limitation, dielectrics, metals, and metals coated with dielectric.

Apparatus 100 further comprises a vacuum 140, which removes gas from apparatus 100. In one embodiment, the vacuum removes gas from the apparatus to a pressure between 0.01 and 730 torr. In another embodiment, the vacuum removes gas from the apparatus to a pressure of between 0.01 and 10 torr. In yet another embodiment, the vacuum removes gas from the apparatus to a pressure of between about 500 and 1,000 mTorr.

In the embodiment shown in FIG. 1a, vacuum 140 connects to chamber 120 via a hose and port and removes gas from chamber 120. As one of ordinary skill in the art will understand, vacuum 140 may evacuate gas from chamber 120 via various airtight pathways (including intermediate pathways) between chamber 120 and vacuum 140. In an alternative embodiment (not shown), the apparatus further includes a valve that seals the port. In an embodiment where the hopper 105 is airtight, the vacuum may also connect to the hopper 105. In yet another embodiment, the vacuum is provided separately from the apparatus.

Apparatus 100 further comprises a gas supply 145. Gas supply 145 connects to chamber 120 via a hose and port and provides gas to chamber 120. In one embodiment, the gas supply provides a variety of gasses to the chamber, including without limitation, air, water vapor, nitrogen, oxygen, argon, hydrogen, noble gasses, and various combinations thereof. In another embodiment, the gas supply provides nitrogen and oxygen in various combinations. In a different embodiment, the gas supply provides ambient gas to the chamber.

As one of ordinary skill in the art will understand, the gas supply may provide gas to the chamber via various airtight pathways (including intermediate pathways) between the gas supply and chamber. In an alternative embodiment (not shown), the apparatus further includes a valve that seals the port. In another alternative embodiment, the gas supply and vacuum share a port. In yet another embodiment, the gas supply is provided separately from the apparatus. An exemplary flow rate is, without limitation, 0-2,000 sccm.

Apparatus 100 further comprises at least a first electrode 150 and a second electrode 155. First electrode 150 and second electrode 155 are powered by an RF generator. The electrodes are located on an opposite sides of exterior surface of chamber 120. The RF frequency generated ranges from 0.2 to 220 MHz, corresponding to a plasma density between about $n_e \times 10^8$-$n_e \times 10^{12}$ or 0.001 to 0.4 W/cm$^3$. The electrodes may be used to generate capacitively coupled plasma, helicon, helicoil, inductively coupled plasma, or a combination of the aforementioned. The electrodes are used in conjunction with a plasma control unit and RF circuit matching network (discussed below). In an alternative embodiment (not shown), the electrodes are separate from the apparatus and do not form a part of the apparatus.

Apparatus 100 further comprises a temperature control unit 160. In FIG. 1*a*, temperature control unit 160 is depicted as a block temperature display; one of ordinary skill in the art will understand that temperature control unit 160 comprises a temperature sensor 165, a processor 170 that regulates temperature, and a temperature control element 175 (temperature control element 175, which is shown in FIGS. 2*a-c*, is omitted from FIG. 1). In one embodiment, the temperature control unit holds temperature within the chamber and on most surfaces between room temperature (20-26° C.) and 50° C. In another embodiment, the temperature control unit holds temperature within the chamber between room temperature and 45° C. In a different embodiment, the temperature control unit holds temperature within the chamber between 0° C. and room temperature.

Temperature sensor 165 senses the temperature in chamber 120. Suitable sensors include, without limitation, analog and digital sensors. In an alternative embodiment (not shown), the temperature sensor senses the temperature of a component of the apparatus, such as a chamber wall, which is then used to estimate the temperature in the chamber.

Processor 170 is programmed to control the temperature of the chamber. A desired chamber temperature is selected and then input into the processor 170. Processor 170 obtains or receives the temperature from temperature sensor 165, and then compares the temperature to the desired chamber temperature. If the desired chamber temperature is lower than the sensed temperature, then processor 170 sends a signal to temperature control element 175 to adjust the temperature utilizing the control devices in the system. If the desired chamber temperature is higher than the sensed temperature, then processor 170 sends a signal to temperature control element 175 to turn off (passive cooling). In an alternative embodiment, if the desired chamber temperature is higher than the sensed temperature, then processor 170 sends a signal to temperature control element 175 to remove energy from the system (active cooling). In another embodiment, the processor sends a signal to the temperature control element without receiving the sensed temperature.

Apparatus 100 further includes a collector 180. Collector 180 channels agricultural matter that has passed through chamber 120. As shown, collector 180 is a cone-shaped funnel. In an alternative embodiment (not shown), the collector is a pyramid-shaped funnel. In another embodiment, the collector is a rectangular receptacle. As one of ordinary skill in the art will understand, a variety of structures may be used for the collector.

Apparatus 100 further includes a second load lock seal 185. Collector 180 bridges load lock seal 185 and chamber 120, although collector 180 need not bridge the second load lock seal 185 and chamber 120. Similar to load lock seal 110, second load lock seal 185 allows agricultural matter to exit chamber 120 without breaking vacuum conditions in chamber 120.

Apparatus 100 further comprises an actuator 190. In one embodiment, actuator 190 ultrasonically vibrates at least one first insert 125, a plurality of first inserts 125, at least one second insert 135, a plurality of second inserts 135, or a combination of the inserts. In a second embodiment, actuator 190 moves apparatus 100 or any subpart, thus promoting the movement of agricultural material through apparatus 100. As one of ordinary skill in the art will understand, in this embodiment, actuator 190 may be configured to, without limitation, rock, vibrate, or rotate apparatus 100. Apparatus 100 and actuator 190 may also be configured so that certain components of apparatus 100 move while other components remain still or relatively still. In additional alternative embodiments, the chamber or components of the apparatus are vibrated mechanically.

Apparatus 100 further comprises a hood 195. Hood 195 prevents ambient matter from interacting with matter exiting chamber 120. Hood 195 is an inverted cone. In an alternative embodiment (not shown), the hood further comprises a bag attachment. In additional embodiments, the hood is a pyramid-shaped funnel or a rectangular chute. As one of ordinary skill in the art will understand, a variety of structures may be used for the hood.

FIG. 1*b* is a perspective view of one embodiment of a first insert 125 with an aperture 130.

FIG. 1*c* is a perspective view of one embodiment of a second insert 130. Second insert 130 features a slope to a central collection exit point that directs agricultural material movement to the next insert below.

Figure 1D:
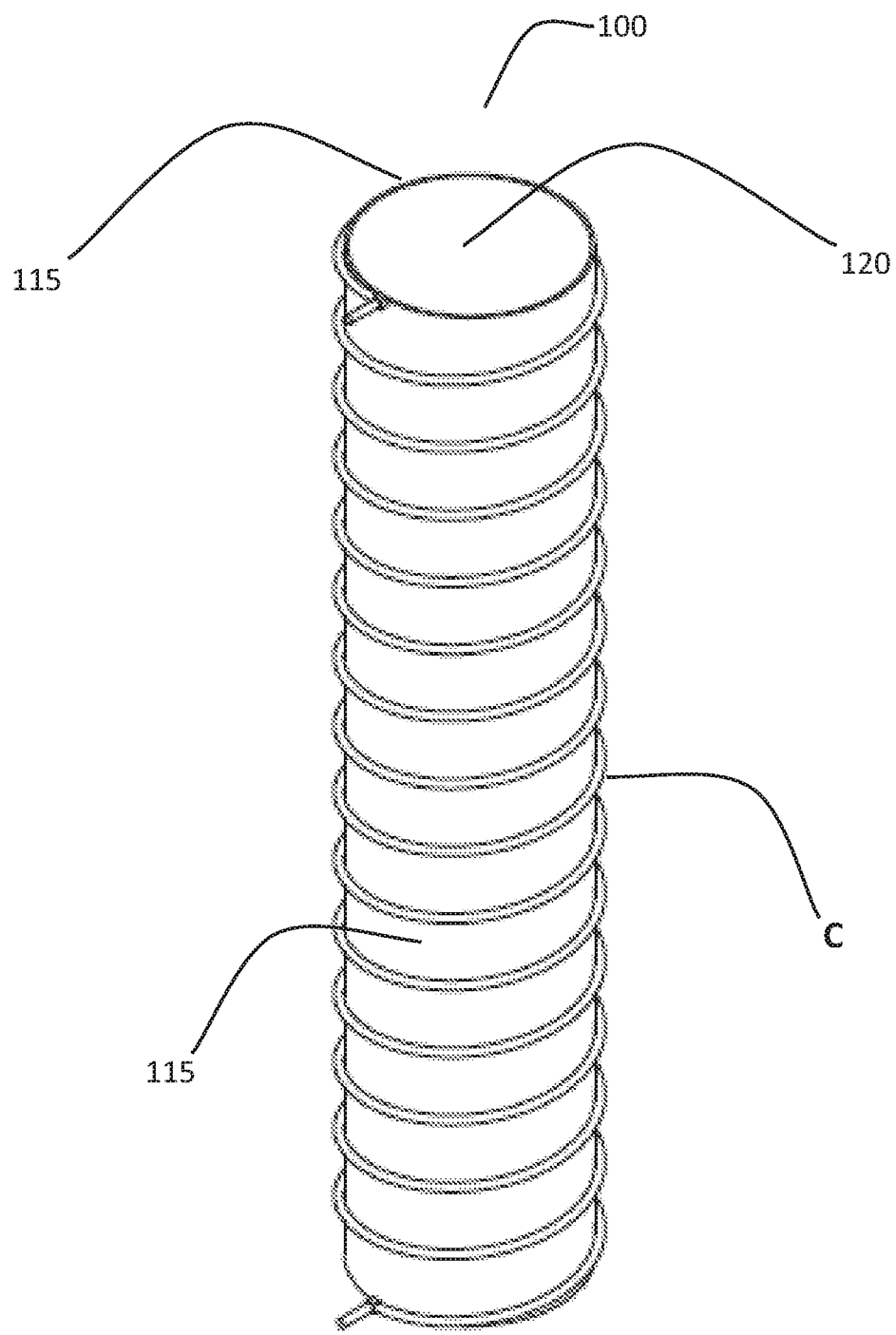
FIG. 1d is a perspective view of one embodiment of an apparatus utilizing a coil.

FIG. 1*d* is a perspective view of one embodiment of an apparatus 100 that features a coil C. The coil winds around the chamber and is used in applications utilizing inductive plasma generation techniques. Various elements depicted in FIG. 1*a* are omitted for simplification.

FIG. 2*a* is a perspective view of an embodiment of the temperature control element 175 for use in the apparatus 100 shown in FIG. 1*a*. While inserts 125, 135 from apparatus 100 are shown, various elements depicted in FIG. 1*a* are omitted for simplification.

Temperature control element 175 features at least one supply line 205*a*. Supply line 205*a* runs vertically and contains a circulating bath fluid (the connection between the line at the top of the apparatus and the line on the side of the apparatus is not shown). Optionally, a second supply line 205*b* may be used to deliver a circulating bath medium. In an alternative embodiment (not shown), a supply line spirals with respect to the vertical direction. One of ordinary skill in the art will understand that a suitable medium for the circulating bath includes, without limitation, liquid, steam, or gas.

Temperature control element 175 further features a plurality of feeder paths 210. The feeder paths 210 extend annularly from the supply lines 205 into the chamber. In one embodiment, the feeder paths extend linearly from a supply line until forming an annulus. In another embodiment, the feeder paths extend annularly. The elements of the temperature control element 175, such as the supply line 205 or the feeder paths 210, may be used to support the inserts.

In a specific embodiment (not explicitly shown in FIG. 2*a*), at least one supply line 205 or one feeder path 210 of the temperature control element 175 connects into at least one first insert 125. Alternatively, a plurality of feeder paths 210 connect into a plurality of first inserts 125. The supply line 205 or feeder paths 210 may also connect into at least one second insert 135 or a plurality of second inserts 135.

In another embodiment (also not shown), the fluid in a temperature-controlled circulating bath can be run through or around, without limitation, a volume associated with the housing, the chamber, and the inserts.

FIG. 2*b* is a front elevational view of an alternative embodiment of the temperature control element 175 shown in FIG. 2*a*. In comparison to FIG. 2*a*, the feeder path 210 shown in FIG. 2*b* connects into at least one first insert 125. Thus, in this embodiment, the fluid within the feeder path also circulates into at least one first insert 125.

FIG. 2*c* is an isometric view of an alternative embodiment of the temperature control element shown in FIG. 2*a*. In comparison to FIG. 2*a*, the feeder path 210 shown in FIG. 2*c* runs down the center of the apparatus.

FIG. 2*d* is a perspective view of an alternative embodiment of select components utilized in a treatment apparatus 200. Various elements from the apparatus 100 depicted in FIG. 1*a* are omitted for simplification.

In FIG. 2*d*, apparatus 200 features a first connection 215 and a second connection 220 that extend from apparatus 200. First connection 215 and second connection 220 are connected to an RF generator (not shown). First connection 215 also connects to first line 225, which extends axially down an outer section of apparatus 200 (the connection between first connection 215 and first line 225 is not depicted). Second connection 220 also connects to second line 230, which extends axially down an outer section of apparatus 200. In the illustrated embodiment, connections 215, 220 and lines 225, 230 are made of conductive materials. Like first electrode 150 and second electrode 155, the first line 225 and second line 230 may be used in connection with other components to generate plasma.

In another embodiment, the first inserts 125 connect to the first line 225, and the first inserts 125 are utilized for an internal RF connection, to generate plasma. When connected in this manner, the first inserts 125 are charged independently of the second inserts 135. Optionally, the second line 230 may be connected to the second inserts 235 for plasma generation purposes. As one of ordinary skill in the art will understand, connections to ground have been omitted for simplicity.

FIG. 2*e* is a front elevational view of an alternative embodiment of the select components utilized in a treatment apparatus 200 shown in FIG. 2*d*. In comparison to FIG. 2*d*, only the first line 225 is shown, and it is shown as connecting to a first insert 125 at connection 240.

Figure 2F:
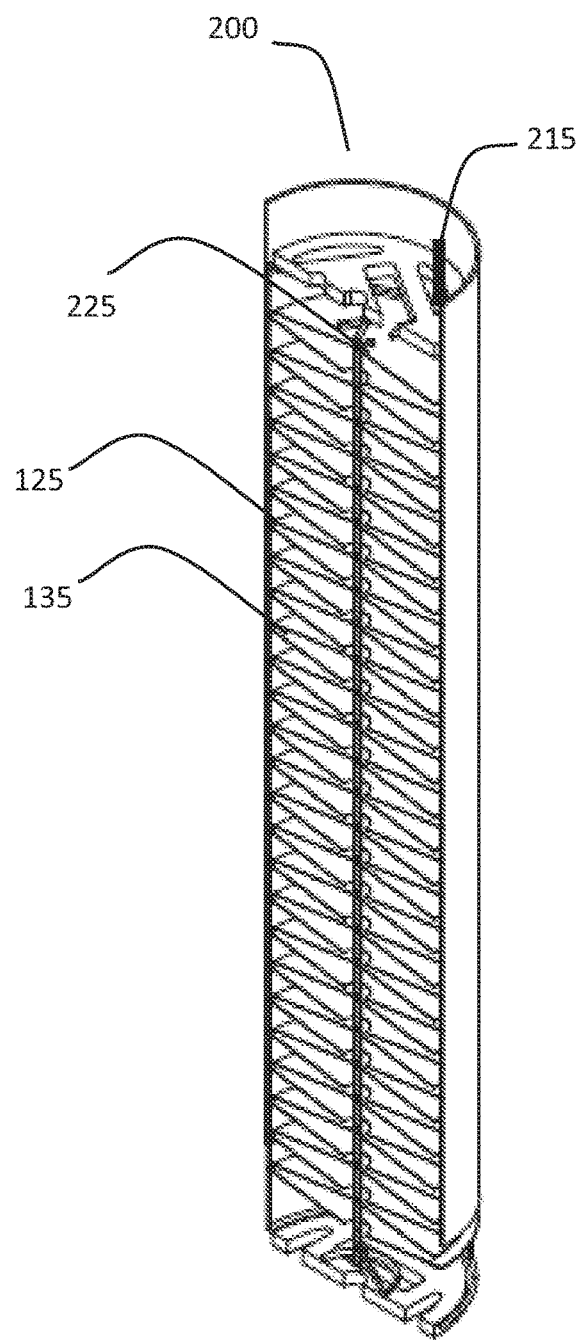
FIG. 2f is an alternative embodiment of the components shown in FIG. 2d and FIG. 2e.

FIG. 2*f* is an isometric view of an alternative embodiment of the select components utilized in a treatment apparatus 200 shown in FIG. 2*d*. In comparison to FIG. 2*d*, only the first line 225 is shown, and it is shown as running down the center of apparatus 200.

Figure 3:
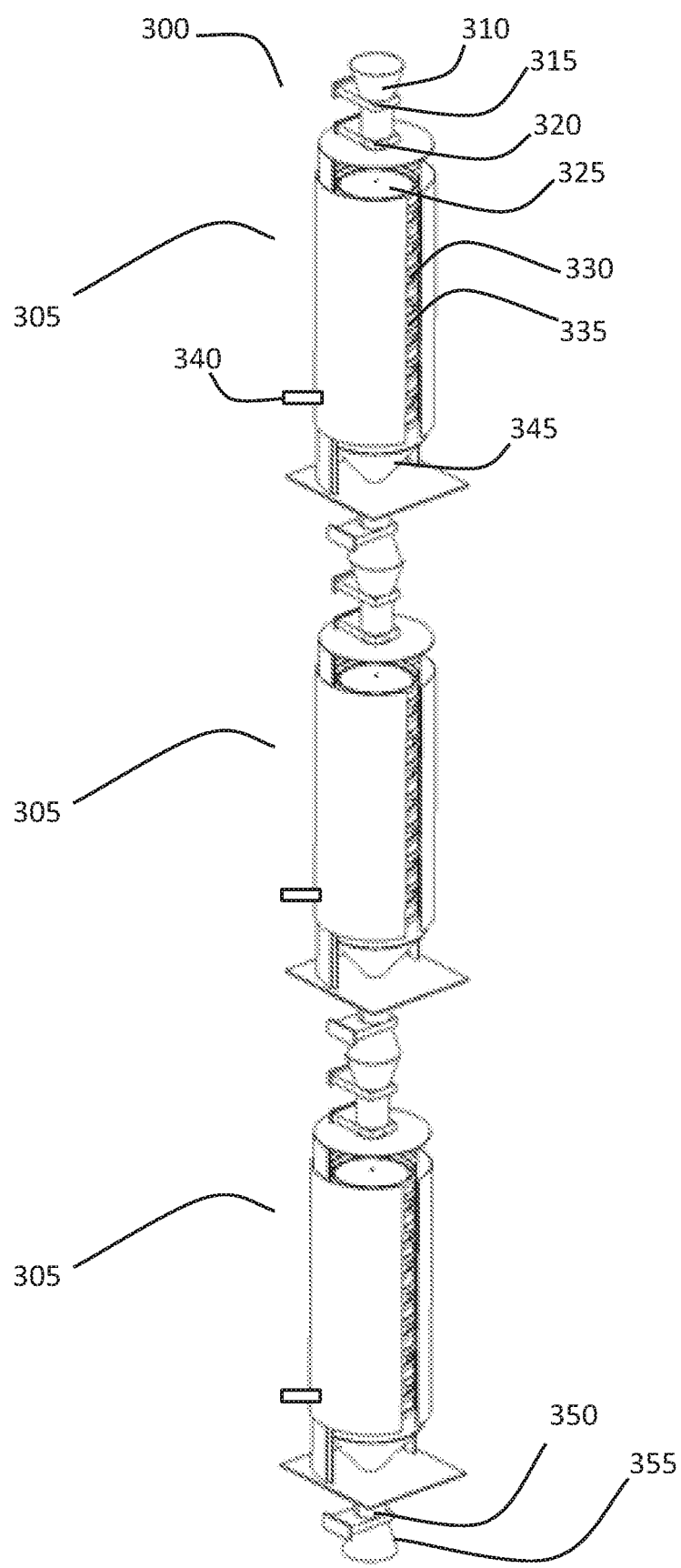
FIG. 3 is a perspective view of one embodiment of a modular treatment apparatus.

FIG. 3 is a perspective view of one embodiment of a modular treatment apparatus 300. Modular treatment apparatus 300 comprises, inter alia, treatment modules 305. Each treatment module 305 may include any of the components discussed above. As shown, modular treatment apparatus 300 features three treatment modules 305. In an alternative embodiment (not shown), the modular treatment apparatus features two treatment modules. In another embodiment, the modular treatment apparatus features four treatment modules. In additional embodiments, the modular treatment apparatus features five or more treatment modules. In a different embodiment, the modular treatment apparatus features a single (replaceable) treatment module. As one of ordinary skill in the art will understand, the treatment modules in modular treatment apparatus need not be identical.

Modular treatment apparatus 300 features a holding receptacle 310. Agricultural matter is placed into holding receptacle 310. Holding receptacle 310 is a simple receptacle with no sensors, agitators, or regulators. In an alternative embodiment (not shown), the holding receptacle features a sensor that measures the amount of agricultural material in the receptacle. The sensor may be digital or analog. In another embodiment, the holding receptacle features an agitator that agitates agricultural material in the receptacle. Examples of agitators include, without limitation, stirrers, vibratory actuators, and pneumatic agitators. In yet another embodiment, the holding receptacle includes a regulator, such as a wheel, that regulates the amount of agricultural material that enters a treatment module. In further embodiments, the holding receptacle contains a combination of sensors, agitators, and regulators.

Modular treatment apparatus 300 further comprises a first seal 315. First seal 315 is resealable, airtight, and distal to treatment module 305. First seal 315, as shown, is disposed between holding receptacle 310 and treatment module 305. In an alternative embodiment (not shown), the first seal is incorporated into at least one treatment module. In another embodiment, the first seal is incorporated into the holding receptacle.

Module 305 further comprises an inlet 320 and a chamber 325. Inlet 320, as shown, is a cylindrical passageway disposed between holding receptacle 310 and chamber 325 of treatment module 305. Inlet 320 is airtight and distal to treatment module 305. Optionally, inlet 320 may be sealable. In an alternative embodiment (not shown), the inlet is formed in a treatment module wall and does not extend from the treatment module. In another embodiment, the cross sectional area of the inlet opening is adjustable. As one of ordinary skill in the art will understand, the inlet may be made of a variety of materials, including without limitation, ceramic, glass, plastic, quartz, rubber, or zirconia.

As shown, chamber 325 is an airtight cylinder, yet chamber 325 is not limited to a cylindrical form. Regardless of the shape of chamber 325, chamber 325 is durable enough to withstand low pressure environments and the creation and containment of plasma. Suitable materials for chamber 325 include, without limitation, quartz, glass, plastic, ceramic, and metal. In an alternative embodiment (not shown), the chamber further includes a cage. In another embodiment, the chamber further includes an opening that allows access to the chamber.

Treatment module 305 features porous discs 330. The perimeter of each porous disc 330 is coextensive with the interior of the chamber 325, but the perimeter of porous disc 330 does not need to be coextensive with the interior of chamber 325. Porous discs 330 are suspended within the interior of chamber 325, and porous discs 330 may be secured by attachment to an internal, axial column (not shown). In an alternative embodiment, the porous discs rest on cantilevers. The cantilevers may extend into the chamber from an external wall or an internal, axial column. In yet another embodiment, the porous discs slide into a structure having compartments that is disposed within the treatment module or chamber.

Each porous disc 330 is sloped so that gravity pulls agricultural matter through the chamber. Varying the slope of the porous disc between adjacent plates allows agricultural matter to be directed through different regions of the chamber (e.g., from an interior toward a perimeter, and vice versa). Likewise, varying the slope of the porous disc allows agricultural matter to pass through the chamber at different rates. In an alternative embodiment (not shown), each porous disc is flat and motion is applied to modular treatment apparatus 300 so that agricultural material passes through the pores of the porous discs.

Each treatment module 305 contains a plurality of porous discs 330. While FIG. 3 shows each treatment module 305 having multiple porous discs, treatment module 305 does not require a specific number of porous discs, and different treatment modules within modular treatment apparatus 300 can have varying numbers of porous discs. In an alternative embodiment (not shown), at least one solid disc is disposed between two porous discs. In yet another embodiment, the plurality of discs is replaced with a plurality of spokes disposed throughout the chamber.

Each treatment module 305 features at least one pair of electrodes 335. Electrodes 335 are positioned on the exterior of treatment module 305. In the embodiment shown, electrodes 335 are permanently attached to treatment module 305 and connected to the RF power source. In an alternative embodiment (not shown), the electrodes are separate from the treatment module and do not form a part of the treatment module. In another embodiment, multiple electrode pairs are individually associated with two or more treatment modules within the modular treatment apparatus.

As shown, each treatment module 305 also features a port 340. Port 340 is positioned distal to treatment module 305, although it could be positioned anywhere on treatment module 305. In an alternative embodiment (not shown), each treatment module contains two ports—preferably disposed at opposite distal ends of the chamber. In another embodiment, only one treatment module in the modular treatment apparatus contains a port. In a different embodiment, only two treatment modules in the modular treatment apparatus contain ports. As one of ordinary skill in the art will understand, a port can be used to remove gas from the chamber or add gas to the chamber.

Each treatment module 305 also features an egress 345. In the illustrated embodiment, egress 345 is a funnel that is positioned distal to the chamber. Optionally, egress 345 may be sealable. In another embodiment (not shown), the egress is a cylindrical passageway disposed between the chamber and an exterior of treatment module. In an alternative embodiment, the egress is formed in a treatment module wall and does not extend from the treatment module wall. In another embodiment, the cross sectional area of a portion of the egress is adjustable. As one of ordinary skill in the art will understand, the egress may be made of a variety of materials, including without limitation, glass, plastic, rubber, or metal.

Modular treatment apparatus 300 further comprises a second seal 350. Second seal 350 is resalable, airtight, and distal to treatment module 305. Second seal 350, as shown, is disposed between an egress and an exterior of treatment module 305 or modular treatment apparatus 300. In an alternative embodiment (not shown), the second seal is incorporated into at least one treatment module. In another embodiment, the second seal is incorporated into a base.

Modular treatment apparatus 300 also features a base 355. The base provides stability to modular treatment apparatus 300. Agricultural material may exit modular treatment apparatus 300 through the bottom of base 355 or via a side chute (not shown). As one of ordinary skill in the art will understand, a variety of structures may be used for the base, and the base may also be used to house or store various components or materials used in connection with modular treatment apparatus 300.

When multiple treatment modules 305 are used in modular treatment apparatus 300, as shown in FIG. 3, inlet 320 connects to egress 345 to form an airtight pathway between adjacent chambers 325. Inlet 320 and egress 345 feature smooth surfaces (which may be lubricated, for example, with vacuum grease). In an alternative embodiment (not shown), the inlet and egress screw together. In another embodiment, a bridge passage, such as a tube, is used to join adjacent chambers. The bridge may be rigid or flexible, and it may be sealable.

FIGS. 4*a*-*h* are top views of discs and plates 405, which are two types of encumbrance structures.

Figure 4B:
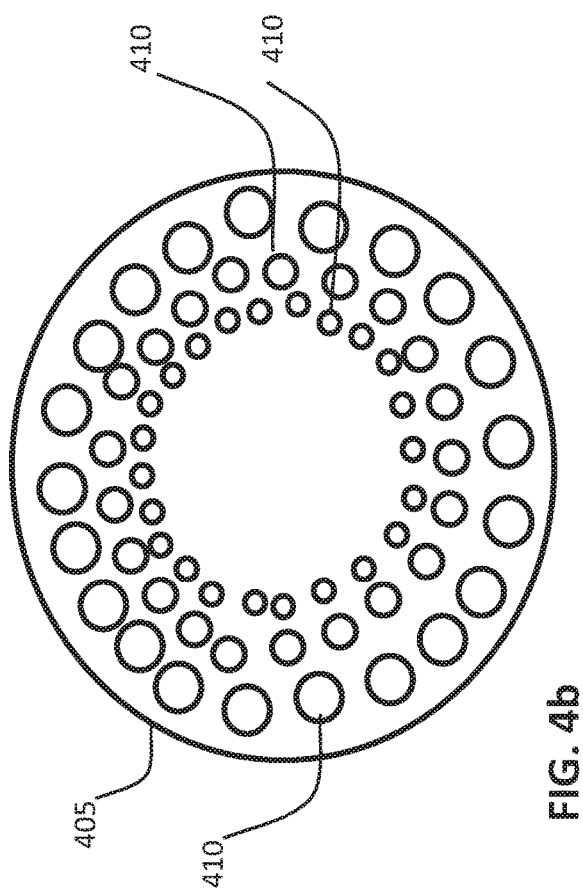
FIGS. 4a-h are top views of discs and inserts used in the apparatuses of FIGS. 1-3.
Figure 4D:
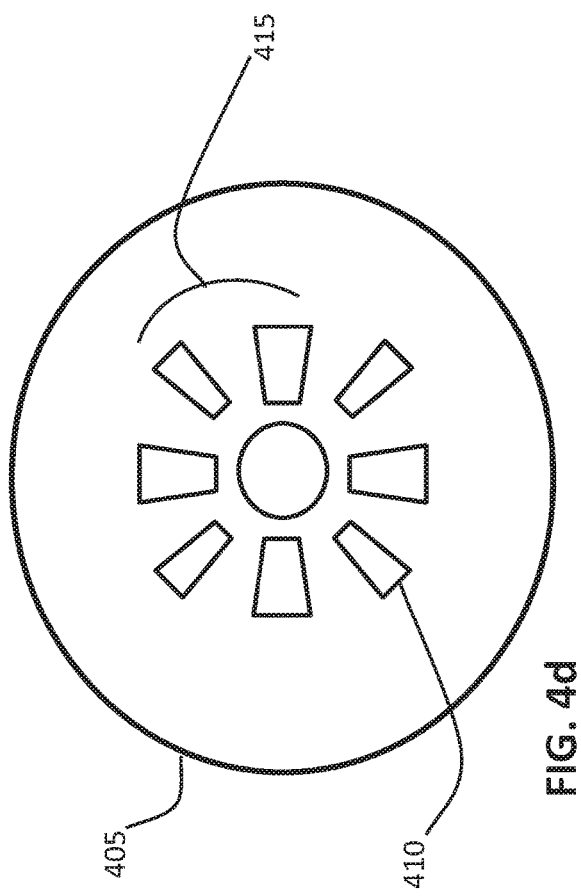
Figure 4A:
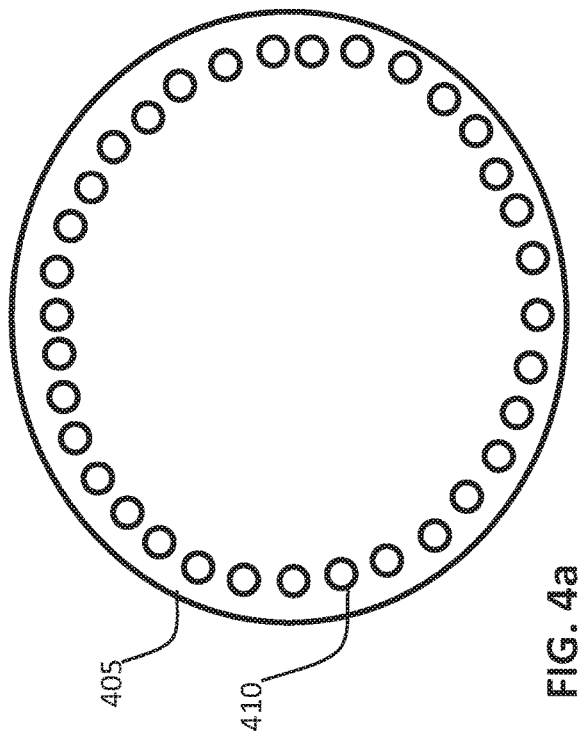

As shown in FIG. 4*a*, the apertures 410 in disc 405 are uniform, circular holes. The apertures 410 are disposed along an interior perimeter of disc 405, and the dimensions of apertures 410 may be selected so that multiple seeds of a given plant species can simultaneously pass through an aperture 410. Alternatively, the dimensions of the apertures may be selected so that only one seed of a given plant species can pass through an aperture at a given time. In an alternative embodiment (not shown), the apertures are randomly disposed throughout the disc.

As shown in FIG. 4*b*, the apertures 410 in disc 405 may vary in size. The large pores allow multiple seeds within a single seed species to pass through the disc, while the small holes allow a single seed within a single seed species to pass through the disc. When the variation in seed size is large between plant species, the disc shown in FIG. 4*b* can be used to accommodate treating multiple plant species without having to change discs 405, because larger seeds will pass over the smaller apertures without passing through a plate. In an alternative embodiment (not shown), all of the apertures are the same size.

Figure 4C:
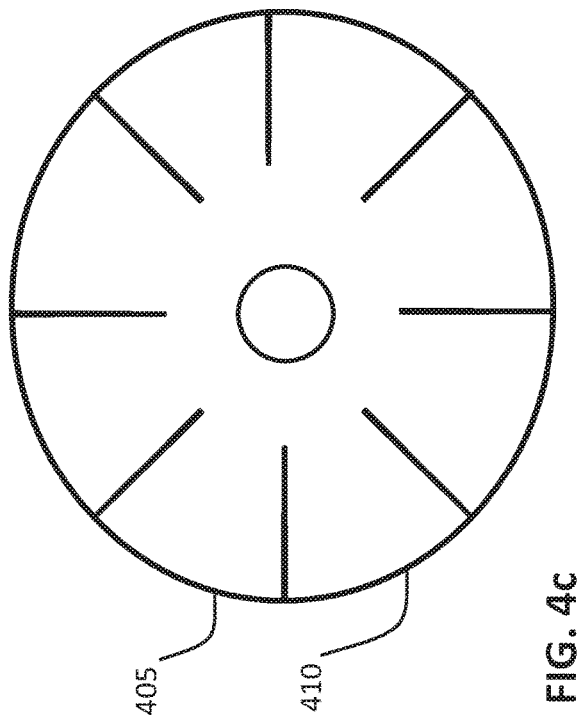

As shown in FIG. 4*c*, the apertures 410 in disc 405 are slits. In alternative embodiments (not shown), the slits may be triangular, rectangular, trapezoidal, or any other similar elongated shape. In an alternative embodiment, two thin discs with slits are stacked on top of each other. At least one disc is rotatable in relation to the other disc, such that the size of apertures may be adjusted. This arrangement allows a user to adjust the apertures without substantial modifications or replacement of various components.

As shown in FIG. 4*d*, the apertures 410 in disc 405 are disposed along an interior ring 415. The interior ring 415 may form part of internal, axial column. Disposing the apertures along an interior ring allows the agricultural material, such as seeds, to move from an outer edge of a disc to an interior edge of the disc. Further, interspersing discs having apertures disposed along an interior ring with discs having apertures disposed along an outer perimeter allows the agricultural material to move across the discs, thus facilitating movement of material.

Figure 4F:
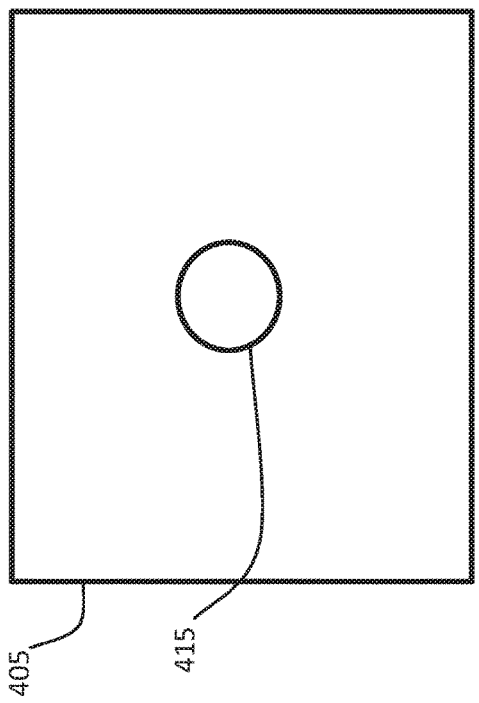
Figure 4H:
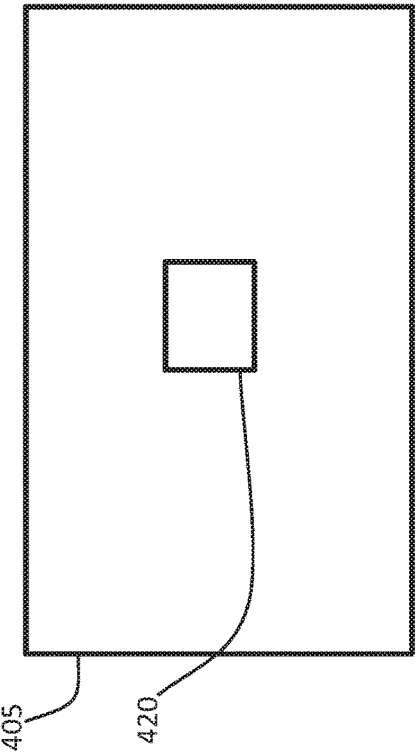
Figure 4E:
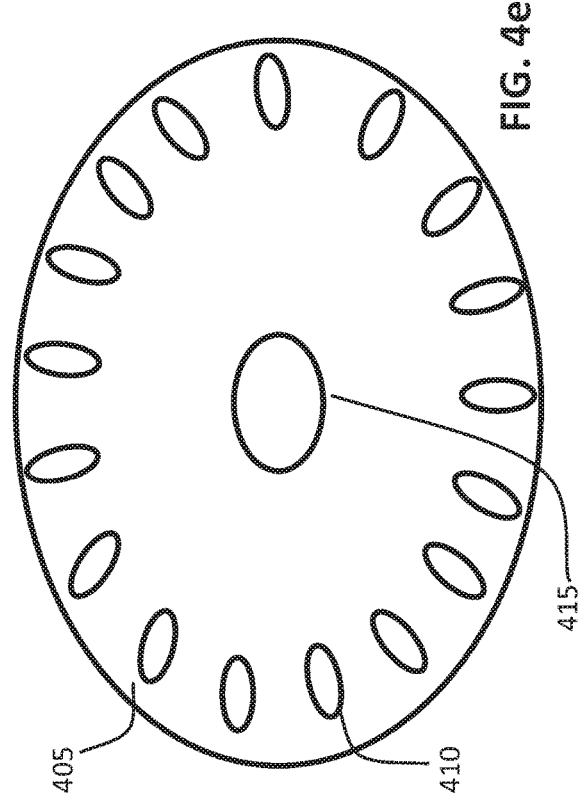

As shown in FIG. 4e, the apertures 410 in disc 405, along with disc 405, may be ovals. Interior ring 415 may also be an oval.

As shown in FIG. 4f, disc 405 may be a square. Disc 405 may also be solid, as shown. When disc 405 is solid, seeds may pass through the disc via a passage along an interior edge ring (not shown) or along an exterior edge ring (also not shown).

Figure 4G:
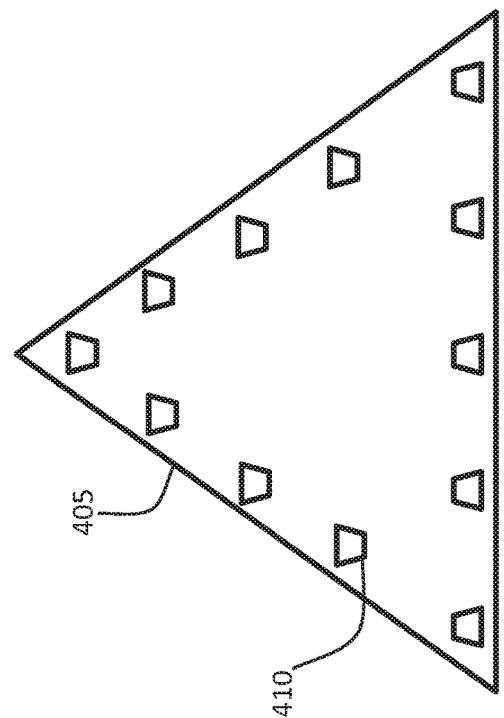

As shown in FIG. 4g, disc 405 is triangular and contains hexagonal apertures 410. The edges of angular discs, such as the example shown in FIG. 4g, may also be rounded.

As shown in FIG. 4h, disc 405 is rectangular and has an interior square 420. Similar to the interior edge ring discussed above, an internal, axial column may be disposed within interior square 420. Alternatively, the area of interior square 415 may be left void.

FIGS. 5a-5d are block diagrams depicting various RF power source systems used to create and maintain capacitively coupled or inductively coupled plasma environments. The RF frequencies generated by RF power sources of FIGS. 5a-5d may range from about 0.2-220 MHz. In one embodiment, a plasma ionization device generates plasma at a frequency range between 11-16 MHz. In another embodiment, the plasma ionization device generates plasma at a frequency range between 0.2-2.0 MHz. In yet another embodiment, the plasma ionization device generates plasma at a frequency range between 25-30 MHz. In a different embodiment, the plasma ionization device generates plasma at a frequency range between 38-50 MHz. Additional frequencies may be utilized with shielding equipment.

Figure 5A:
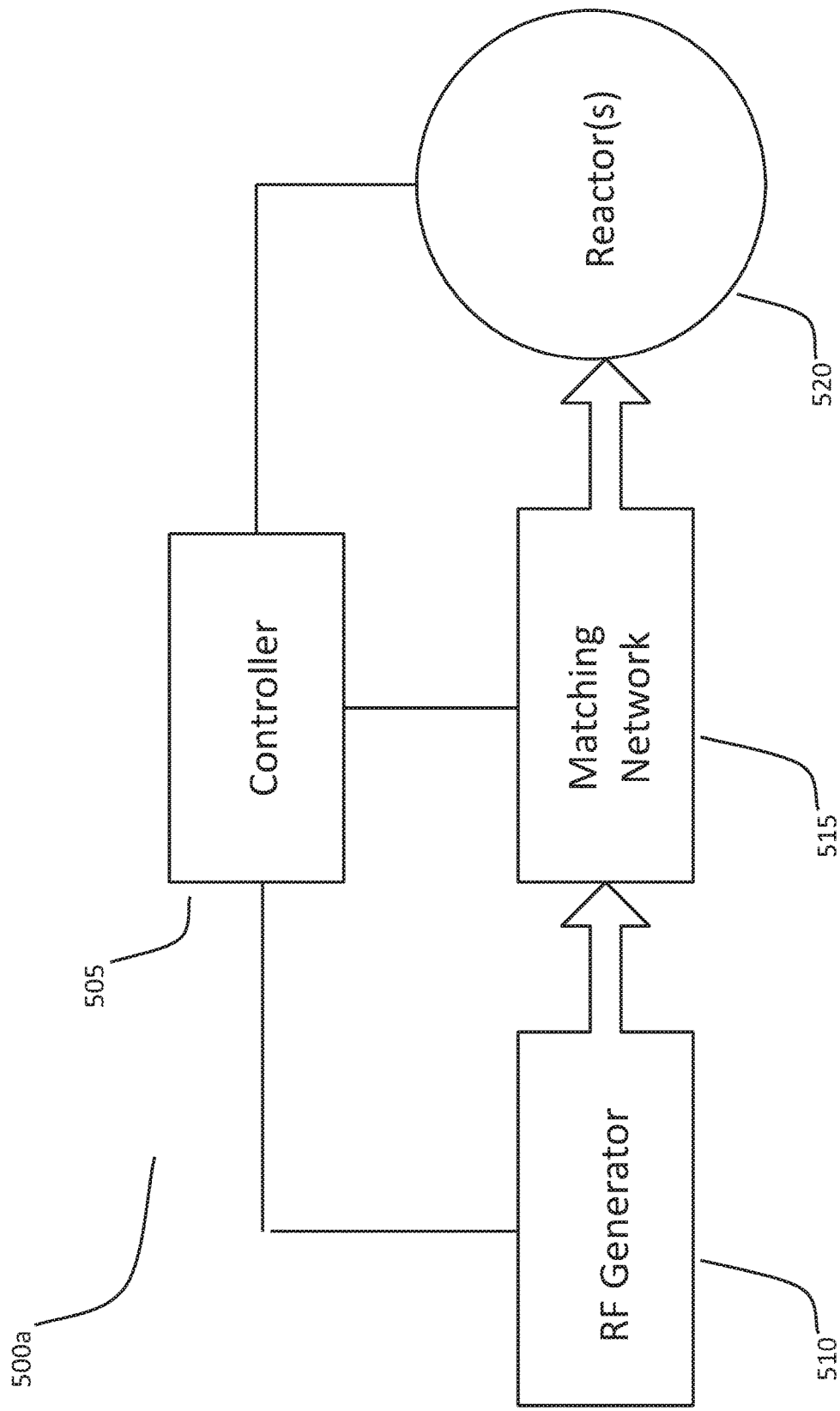
FIGS. 5a-5d are block diagrams depicting RF power source systems used to create and maintain plasma environments.

In FIG. 5a, RF power source system 500a features a controller 505 that controls RF generator 510 and matching network 515. RF generator 510 provides the voltage source to strike gas into plasma. Matching network 515 provides impedance matched to the impedance of the RF generator. As one of ordinary skill in the art will understand, matching the impedance of the network to the impedance of the RF generator optimizes power transfer.

RF power source system 500a strikes the gas within reactor 520 into plasma. Plasma within reactor 520, in turn, is monitored by the controller 505. Similarly, the impedance of matching network 515 is also monitored by controller 505.

Figure 5B:
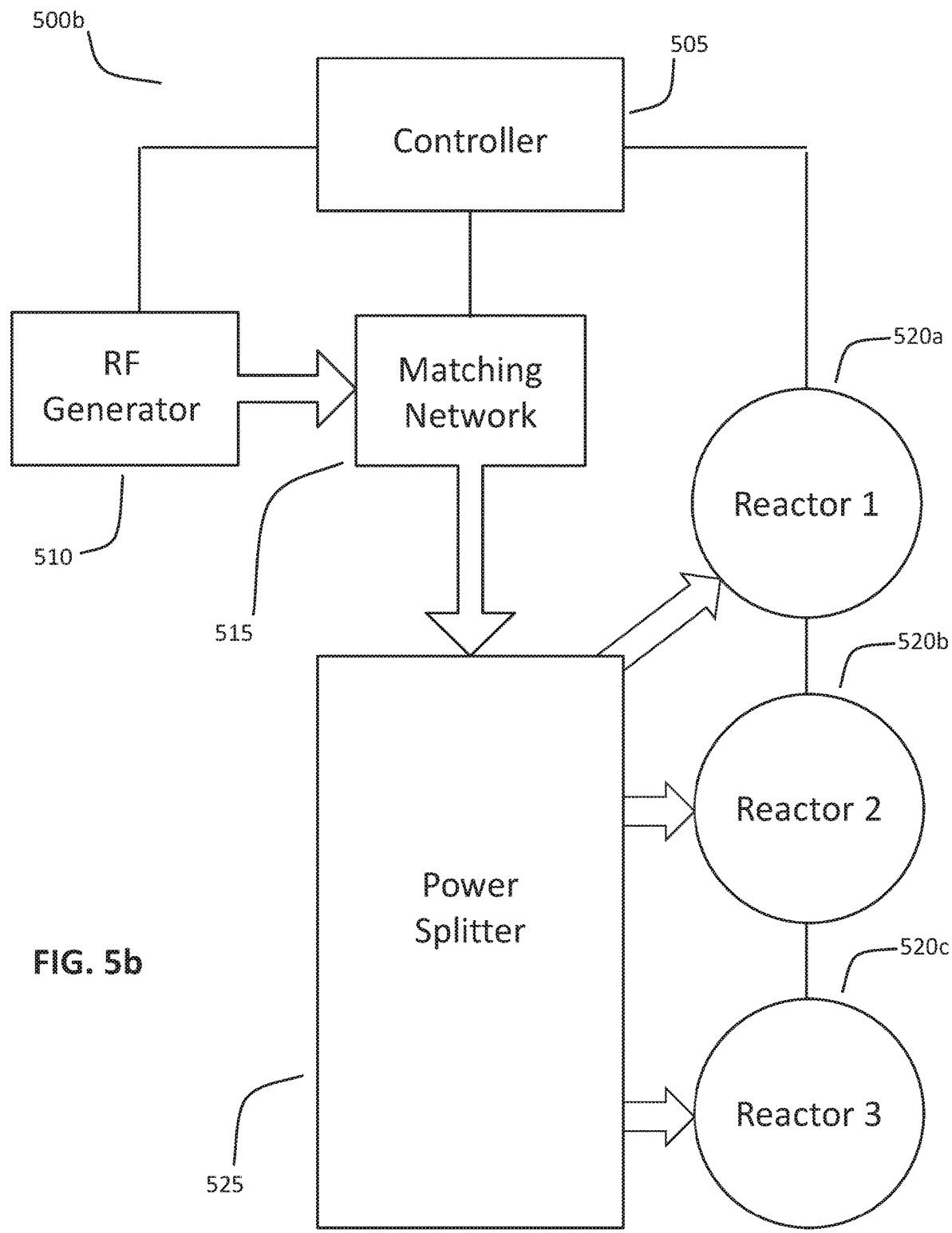

In the embodiment depicted in FIG. 5b, RF power source system 500b creates plasma within a first reactor 520a, a second reactor 520b, and a third reactor 520c. The first, second, and third reactors 520a-c can be operated in series or in parallel.

In the depicted configuration, RF generator 510 and matching network 515 provide a power source that power splitter 525 splits between first reactor 520a, second reactor 520b, and third reactor 520c. Controller 505 monitors the RF generator, the matching network 515, and the reactors 520a-c to ensure optimal plasma conditions at each reactor.

Figure 5C:
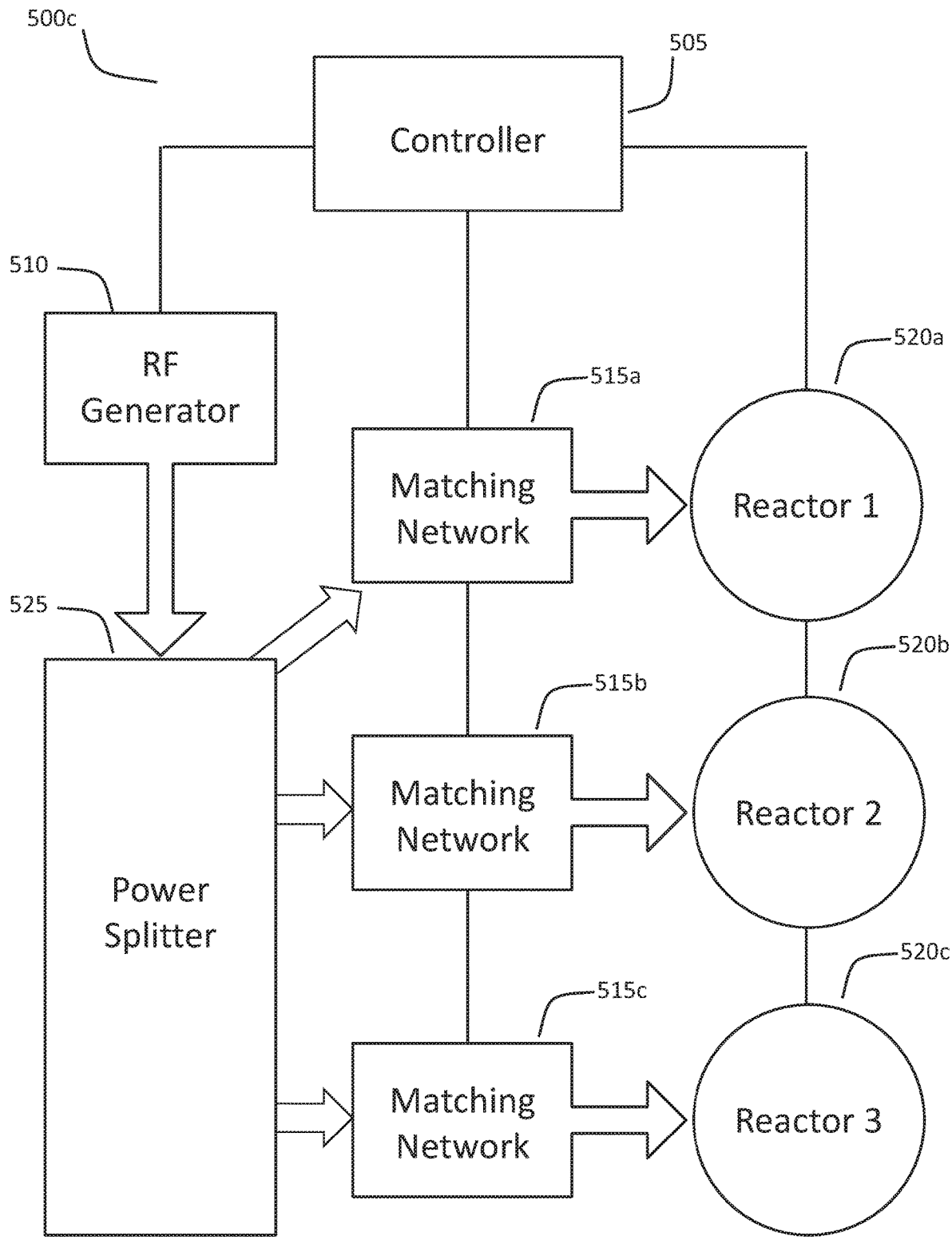

FIG. 5c depicts an RF power source system 500c with additional matching networks that allow for further control functions. In the illustrated embodiment, three matching networks are shown—first matching network 515a, second matching network 515b, and third matching network 515c. In this embodiment, power splitter 525 is disposed between RF generator 510 and the matching networks 515a-c. Each matching network 515a-c pairs with a reactor 520a-c. Matching networks 515a-c and reactors 520a-c may be connected in series or in parallel with the controller 505.

Figure 5D:
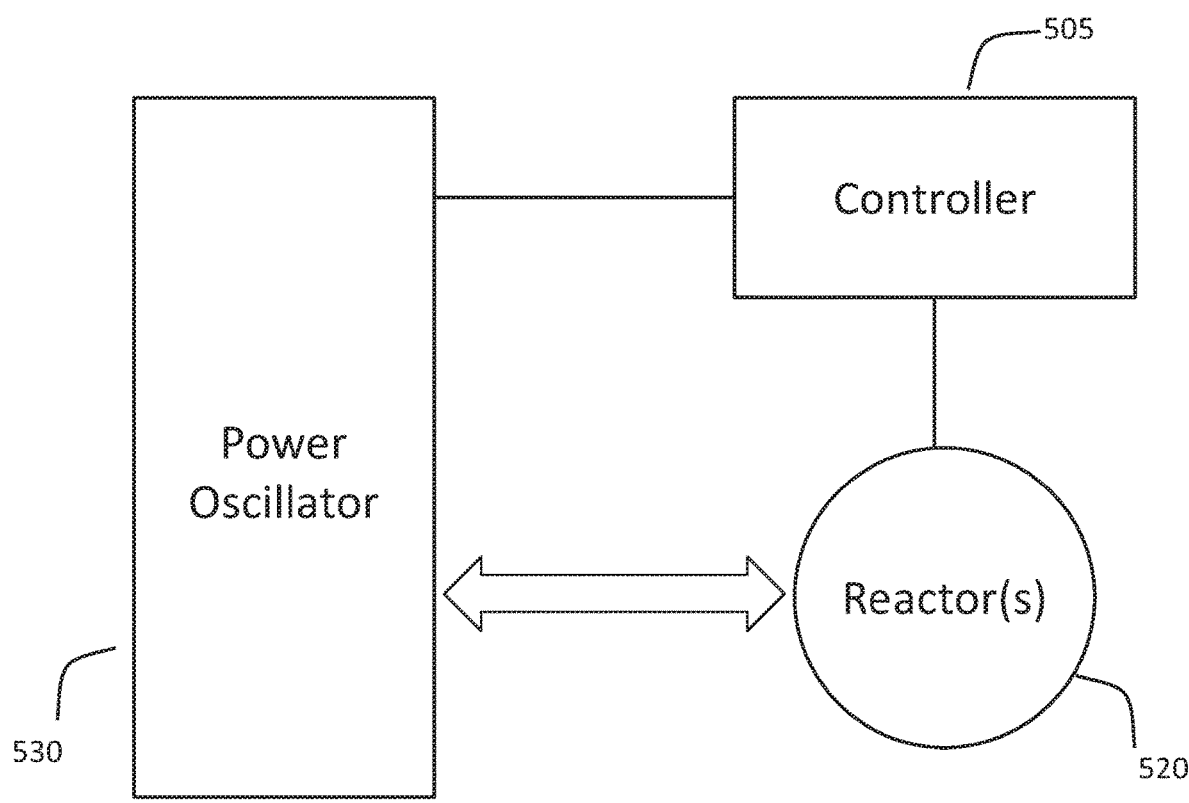

FIG. 5d depicts an RF power source system 500d featuring a controller 505 and a power oscillator 530. When power oscillator 530 is utilized, reactor 520 forms a part of the resonant circuit. In this embodiment, controller 505 mitigates efficiency and frequency control issues.

Figure 6A:
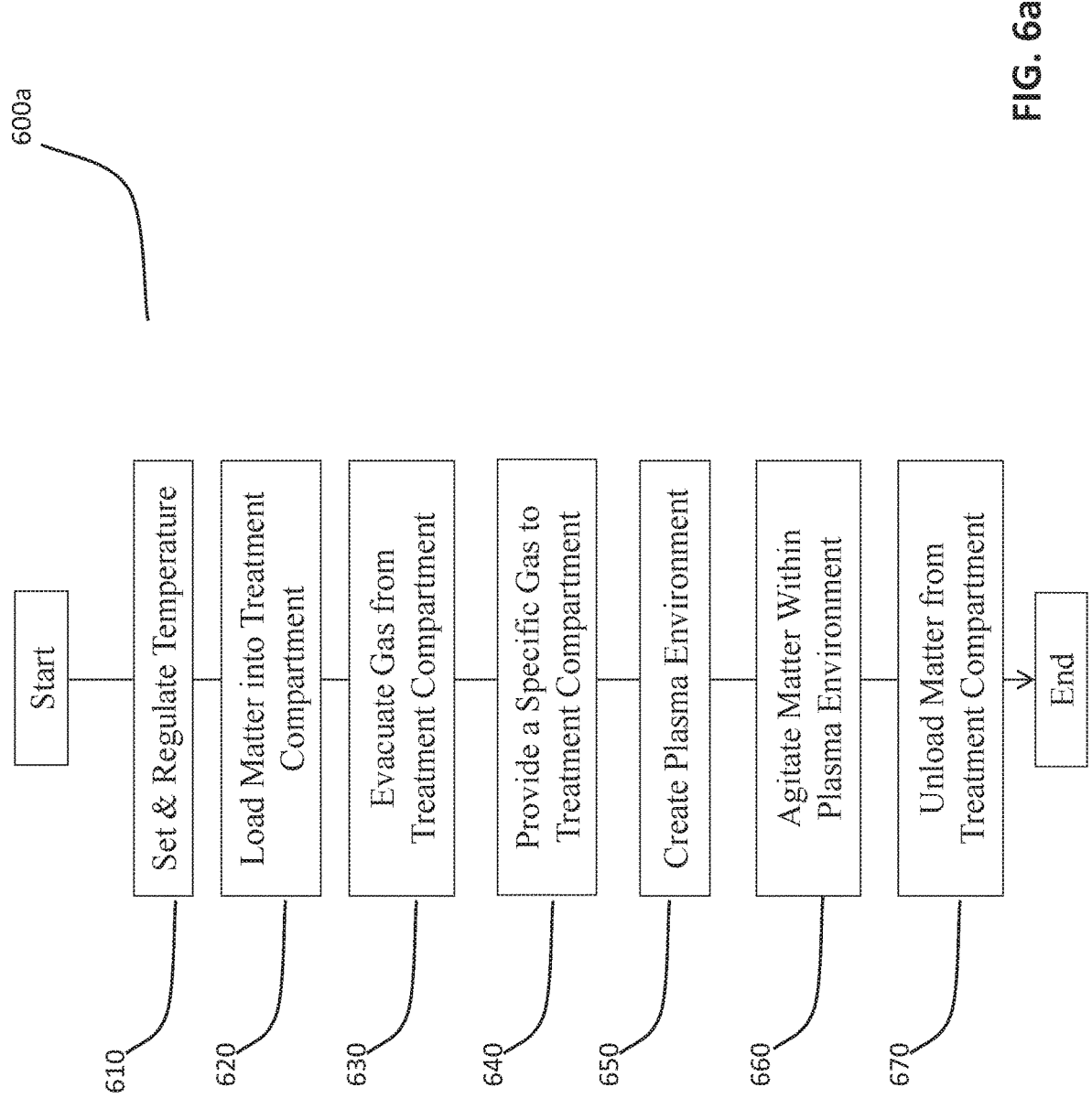
FIGS. 6a-6b are flowcharts depicting generalized processes for treating matter.
Figure 6B:
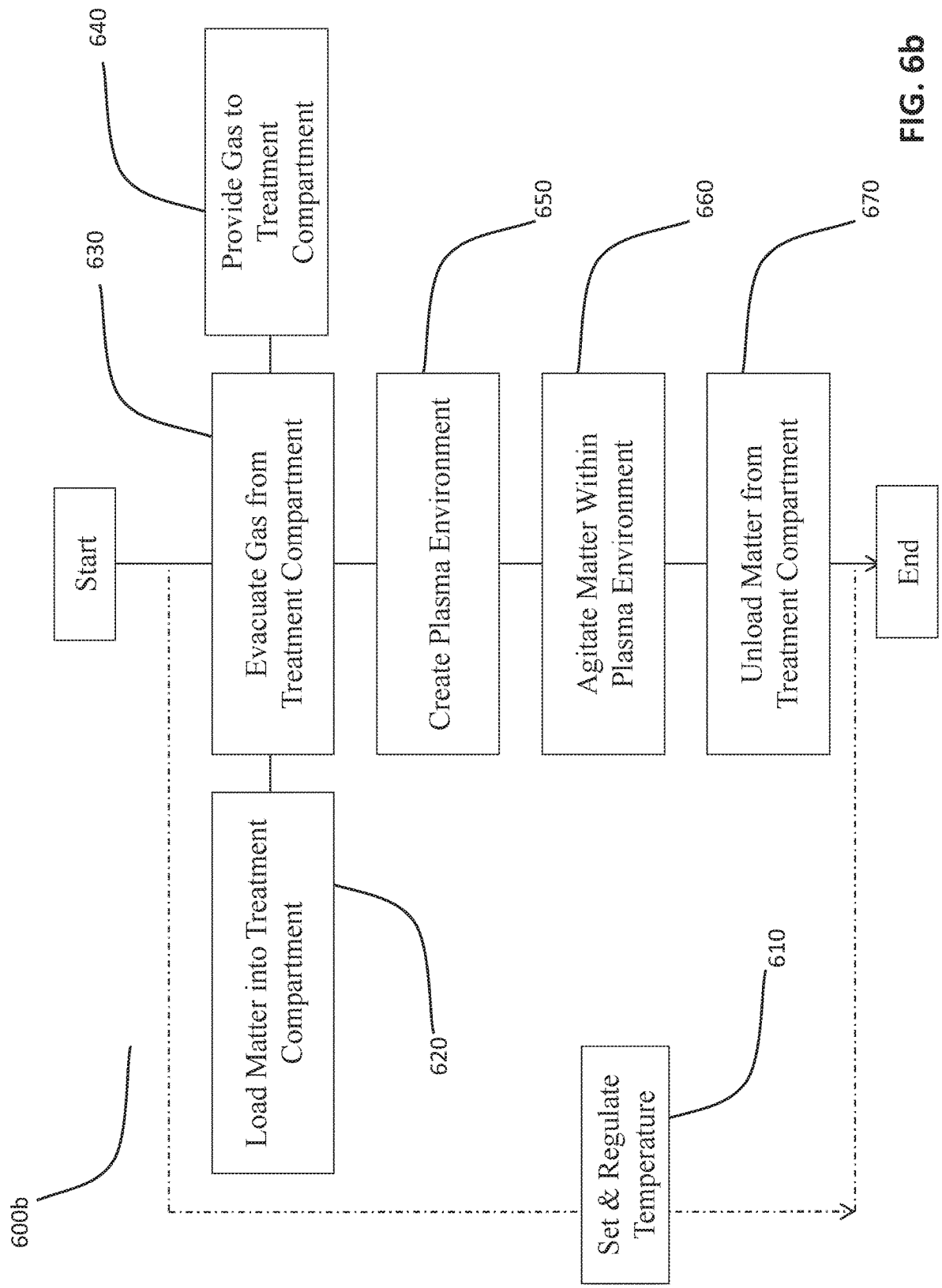

FIGS. 6a-6b are flowcharts describing a generalized processes for treating agricultural matter.

In FIG. 6a, method 600a starts with setting and regulating 610 the temperature in the treatment compartment. In setting and regulating step 610, a temperature control unit is activated. Setpoint regulation, or feedback control, is used to ensure that the temperature remains within a desired range.

Method 600a continues with loading 620 agricultural matter into a treatment compartment. In loading step 620, matter may be loaded from a source external to the treatment compartment or from a source connected to the treatment compartment.

Method 600a then continues with evacuating 630 gas from the treatment compartment. In evacuating step 630, a vacuum is used to remove existing gas from the treatment compartment.

Method 600a then continues with providing 640 a specific gas to the treatment compartment. Exemplary gases and the pressures at which they are provided are discussed above.

After providing step 640 occurs, method 600a continues with creating 650 a plasma environment. In creating step 650, the plasma environment is created using the RF power source systems and electrodes.

Once a plasma environment is created in creating step 650, the matter within the plasma environment is agitated 660. In agitating step 660, the matter may be stirred within the treatment compartment. Alternatively, the matter may be agitated by, without limitation, rocking, vibrating, rotating, or tilting the treatment chamber.

In agitating step 660, the matter within the treatment compartment is treated with plasma. In one embodiment, the surface of the matter is activated such that the contact angle of the matter is increased. In another embodiment, the surface of the matter is activated such that the contact angle of the matter is decreased.

Method 600a then continues, and concludes with, unloading 670 the matter from the treatment compartment. In unloading step 670, material may be, without limitation, directed into packaging or storage, set aside for testing, or directed into another treatment compartment.

FIG. 6b shows an alternative embodiment of method 600a. In method 600b, loading step 620, evacuating step 630, and providing step 640 are performed prior to creating step 650. Loading step 620, evacuating step 630, and providing step 640 may be performed in any order prior to creating step 650, and they may also be performed concurrently. Agitating step 660 and unloading step 670 are then performed subsequent to creating step 650. In method 600b, setting and regulating step 610 (shown in dashed lines) is optional. Setting and regulating step 610 may be performed at any time in connection with method 600b.

Figure 7A:
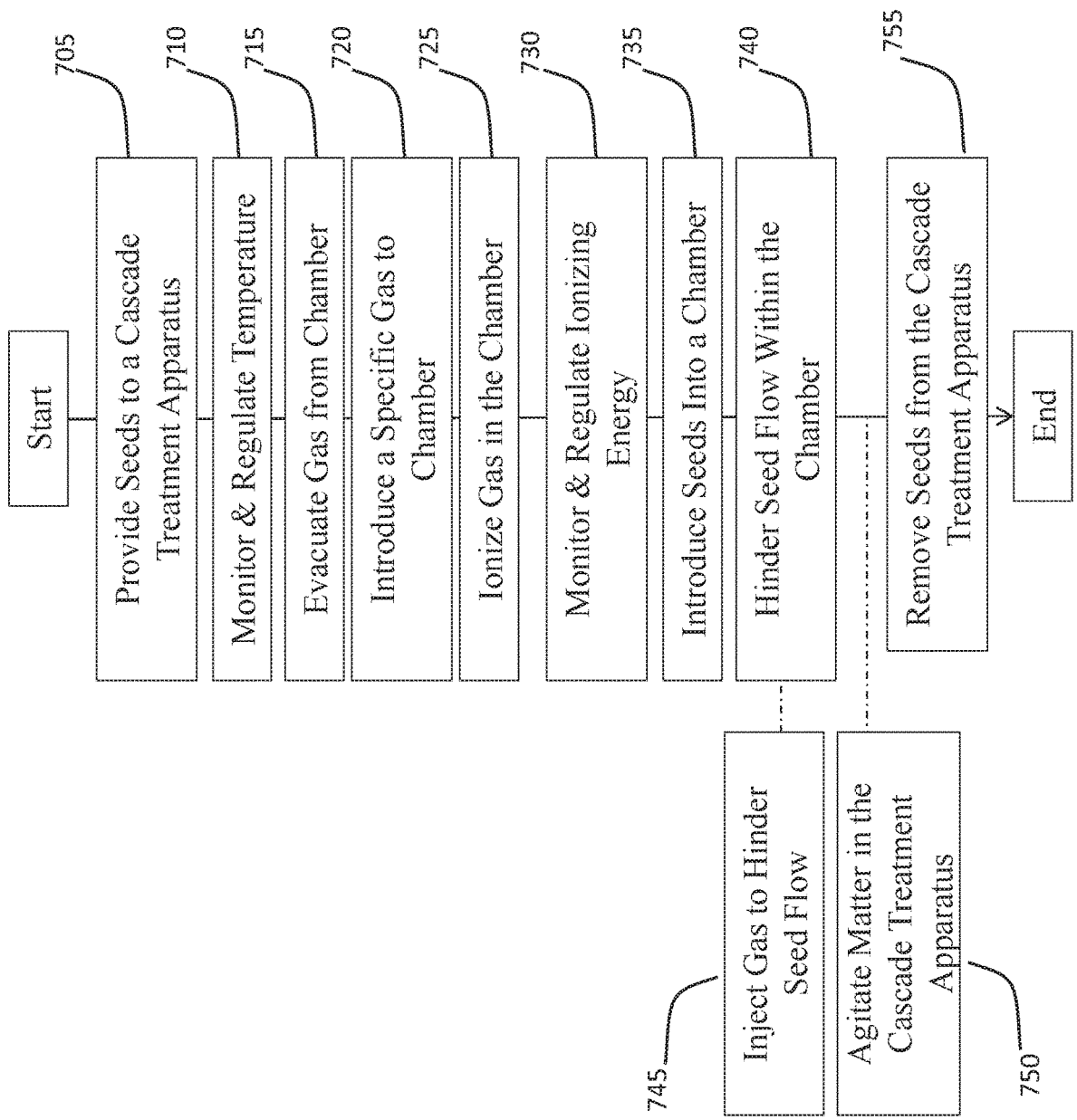
FIGS. 7a-7b are flowcharts depicting processes for treating matter using a cascade treatment apparatus.
Figure 7B:
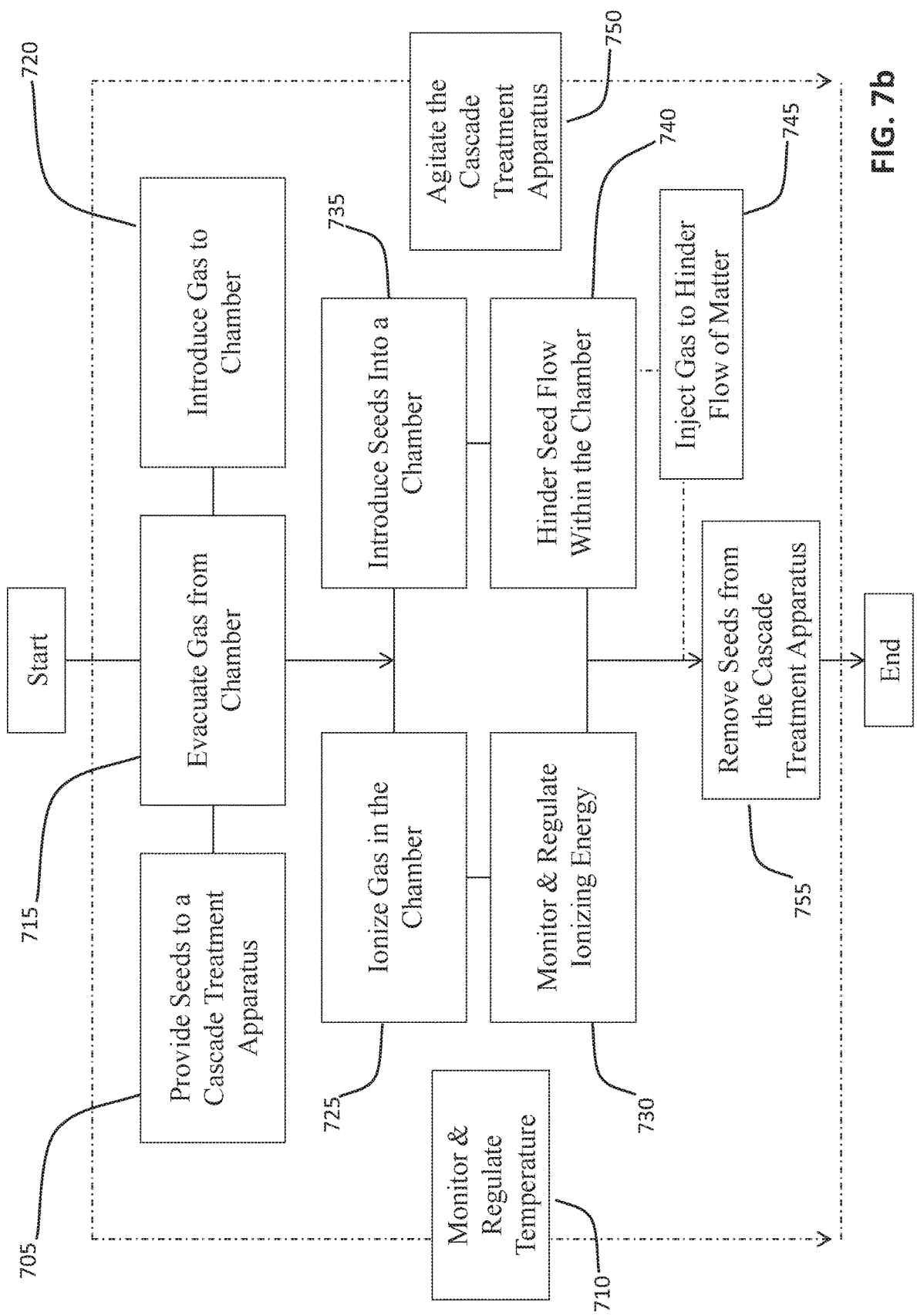

FIG. 7a and FIG. 7b are flowcharts describing processes for treating agricultural matter using a cascade treatment apparatus.

In FIG. 7a, method 700a starts with providing 705 seeds to a cascade treatment apparatus. In providing step 705, seeds may be provided (continuously or semi-continuously) to a storage receptacle or directly to a treatment chamber.

Method 700a continues with monitoring and regulating 710 the temperature in the cascade apparatus. In one embodiment, the temperature in the treatment chamber may be monitored and regulated. In another embodiment, a temperature sensor senses the temperature of a component of the apparatus, such as a treatment chamber wall, which is then used to estimate and regulate the temperature in the treatment chamber.

Method 700a then continues with evacuating step 715, introducing step 720, and ionizing step 725. Evacuating step 715, introducing step 720, and ionizing step 725 are substantially similar to evacuating step 630, providing step 640, and creating step 650. After ionizing step 725, method 700a continues with monitoring and regulating 730 the ionizing energy used in ionizing step 725.

Once a plasma environment is created, seeds are introduced 735 into a treatment chamber. In one embodiment of introducing step 735, seeds are introduced in batches. In an alternative embodiment, seeds are introduced continually.

As seeds are introduced in introducing step 735, the flow of seeds within the chamber is hindered 740 with the use of encumbrance structures such as inserts or porous discs. Optionally, gas may be injected 745 through an encumbrance structure to generate a force that momentarily opposes gravity. This force further hinders the flow of seeds within the chamber. Likewise, an optional agitation step 750 may also be practiced as the seeds are introduced or hindered. Agitation step 750 is substantially similar to agitating step 660.

Method 700a then continues, and concludes with, removing 755 seeds from the cascade treatment apparatus. In removing step 755, material may be, without limitation, directed into packaging or storage, set aside for testing, or directed into another treatment compartment. The material may be removed, directed, or set aside continuously or semi-continuously.

FIG. 7b shows an alternative embodiment, method 700b, of method 700a. Like method 600b, method 700b shows that various steps in method 700a may be performed concurrently or in more than one order.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995). Also, to the extent that the terms "in" or "into" are used in the specification or the claims, it is intended to additionally mean "on" or "onto." Furthermore, to the extent the term "connect" is used in the specification or claims, it is intended to mean not only "directly connected to," but also "indirectly connected to" such as connected through another component or components.

While the present disclosure has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art. Therefore, the disclosure, in its broader aspects, is not limited to the specific details, the representative apparatus and method, and illustrative examples shown and described. Accordingly, departures may be made from such details without departing from the spirit or scope of the applicant's general inventive concept.

What is claimed is:

1. A method for treating agricultural matter comprising:
   providing seeds to a cascading treatment apparatus;
   introducing the seeds into a chamber in the cascading treatment apparatus;
   hindering vertical flow of the seeds within the chamber with encumbrance structures;
   evacuating gas from the chamber;
   introducing gas to the chamber;
   ionizing gas introduced into the chamber;
   monitoring and regulating ionizing energy within the chamber;
   monitoring and regulating temperature within the chamber;
   removing the seeds from the cascading treatment apparatus.

2. The method of claim 1, further comprising steps of introducing the seeds into a second chamber in the cascading treatment apparatus, hindering the vertical flow of the seeds within the second chamber with encumbrance structures, evacuating gas from the second chamber, introducing gas to the second chamber, ionizing gas introduced into the second chamber, and monitoring and regulating temperature within the second chamber.

3. The method of claim 1, wherein evacuating gas from the chamber precedes introducing untreated seeds into the chamber.

4. The method of claim 1, further comprising a step of rocking, vibrating, rotating, or tilting the cascading treatment apparatus to facilitate the vertical flow of the seeds within the chamber.

5. The method of claim 1, wherein monitoring and regulating temperature within the chamber is performed via setpoint regulation.

6. The method of claim 1, wherein porous discs are the encumbrance structures used to hinder the vertical flow of the seeds within the chamber.

7. The method of claim 6, further comprising a step of injecting gas through pores in the porous discs to generate a force that momentarily oppose gravity.

8. A method for treating agricultural matter comprising:
   providing seeds to a cascading treatment apparatus;
   introducing the seeds into a chamber in the cascading treatment apparatus;
   hindering a vertical flow of the seeds within the chamber with encumbrance structures;
   evacuating gas from the chamber;
   introducing gas to the chamber to a pressure between 0.001 and 10 torr;
   generating a plasma at the pressure between 0.001 and 10 torr;
   removing the seeds from the chamber.

9. The method of claim 8, wherein the removing of the seeds from the chamber includes transferring the seeds to a second chamber.

10. The method of claim 8, wherein the generating of the plasma includes generating the plasma with an RF power source.

11. The method of claim 10, wherein the RF power source includes a controller that controls an RF generator and a matching network.

12. The method of claim 11, further comprising providing an impedance matched to an impedance of the RF power source.

13. The method of claim 8, further comprising receiving liquid from a temperature-controlled circulating bath.

14. The method of claim 8, further comprising replacing discs in the chamber.

15. A method for treating agricultural matter comprising:
providing seeds into a hopper having an upper opening, a lower opening, and at least one side wall that connects the upper opening and the lower opening;
feeding the seeds from the hopper to an elongated, airtight seed-processing chamber;
removing gas from the chamber;
delivering gas to the chamber;
generating a plasma environment;
regulating temperature in the chamber;
moving the seeds along a plurality of first inserts disposed in the chamber, each first insert having an annular passage and a cross sectional area that substantially coincides with the cross sectional area of the chamber;
moving the seeds along a plurality of second inserts disposed in the chamber, each second insert having apertures and a cross sectional area that substantially coincides with the cross sectional area of the chamber; and
passing the seeds out of the chamber.

16. The method of claim 15, wherein each first insert is curved.

17. The method of claim 16, wherein each second insert is curved opposite of the first insert.

18. The method of claim 15, wherein the moving of the seeds along the plurality of first inserts includes using an actuator.

19. The method of claim 15, wherein the generating of the plasma environment includes using at least one pair of electrodes to generate a plasma environment at a frequency range between 0.2 to 220 MHz.

20. The method of claim 15, wherein the regulating of the temperature in the chamber includes maintaining a chamber temperature of 20-50° C.

\* \* \* \* \*